(12) United States Patent
Wang et al.

(10) Patent No.: US 11,471,326 B2
(45) Date of Patent: Oct. 18, 2022

(54) FOCUSING LIGHT THROUGH CATARACTOUS LENSES

(71) Applicant: California Institute of Technology, Pasadena, CA (US)

(72) Inventors: Lihong Wang, Arcadia, CA (US); Frank L. Brodie, San Francisco, CA (US); Yuecheng Shen, Pasadena, CA (US); Yan Liu, Pasadena, CA (US); Haowen Ruan, Pasadena, CA (US)

(73) Assignees: CALIFORNIA INSTITUTE OF TECHNOLOGY, Pasadena, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 145 days.

(21) Appl. No.: 16/178,190

(22) Filed: Nov. 1, 2018

(65) Prior Publication Data

US 2019/0125583 A1 May 2, 2019

Related U.S. Application Data

(60) Provisional application No. 62/580,339, filed on Nov. 1, 2017.

(51) Int. Cl.
*A61F 9/01* (2006.01)
*A61F 9/008* (2006.01)

(52) U.S. Cl.
CPC ...... *A61F 9/00814* (2013.01); *A61F 9/00817* (2013.01); *A61F 2009/0087* (2013.01); *A61F 2009/00844* (2013.01); *A61F 2009/00863* (2013.01); *A61F 2009/00887* (2013.01)

(58) Field of Classification Search
CPC ......... A61F 9/0079; A61F 9/007; A61F 9/008
See application file for complete search history.

(56) References Cited

U.S. PATENT DOCUMENTS

| 5,880,813 A | 3/1999 | Thall |
| 5,908,394 A | 6/1999 | Kandel et al. |
| 6,003,993 A | 12/1999 | Webb |
| 9,798,147 B1 | 10/2017 | Park et al. |
| 2010/0149487 A1 | 6/2010 | Ribak |
| 2013/0237972 A1* | 9/2013 | Raksi ................ A61F 9/00825 606/6 |

(Continued)

OTHER PUBLICATIONS

PCT International Search Report & Written Opinion dated Feb. 22, 2019, International Application No. PCT/US2018/058734.

(Continued)

*Primary Examiner* — Michael J D'Abreu
(74) *Attorney, Agent, or Firm* — Gates & Cooper LLP

(57) ABSTRACT

A device for irradiating ocular tissue, including a source of electromagnetic radiation; a beacon scattering the electromagnetic radiation transmitted through an opacity in ocular tissue so as to form scattered electromagnetic radiation; a modulator transmitting output electromagnetic radiation having a field determined from a recording of the scattered electromagnetic radiation transmitted through the opacity, so that the output electromagnetic radiation is transmitted through the opacity to the beacon. The device can be used to treat amblyopia or correct optical aberrations in corneal or lens tissue.

21 Claims, 15 Drawing Sheets

(56) References Cited

U.S. PATENT DOCUMENTS

2014/0320805 A1* 10/2014 Wilzbach ............ A61B 3/0025 351/204
2016/0022976 A1* 1/2016 Peyman ............ A61K 47/6929 600/439

OTHER PUBLICATIONS

Gelbart, S.S., et al., "Long-term visual results in bilateral congenital cataracts", American Journal of Ophthalmology, 1982, pp. 615-621, vol. 93, No. 5.

Beller, R., et al., "Good visual function after neonatal surgery for congenital monocular cataracts", American Journal of Ophthalmology, May 1981, pp. 559-565, vol. 91, No. 5.

Khan, A.O., et al., "Age at the time of cataract surgery and relative risk for aphakic glaucoma in nontraumatic infantile cataract", Journal of American Association for Pediatric Ophthalmology and Strabismus {JAAPOS}, 2009, pp. 166-169, vol. 13, No. 2.

Vishwanath, M., et al., "Is early surgery for congenital cataract a risk factor for glaucoma?", Br. J. Ophthalmol., 2004, pp. 905-910, vol. 88, No. 7.

Xu, X., et al., "Time-reversed ultrasonically encoded optical focusing into scattering media", Nature Photonics, Mar. 2011, pp. 154-157, vol. 5, No. 3.

Wang, Y.M., et al., "Deep-tissue focal fluorescence imaging with digitally time-reversed ultrasound-encoded light", Nature Communications, 2012, pp. 1-8, vol. 3, No. 928.

Ruan, H., et al., "Iterative Time-Reversed Ultrasonically Encoded Light Focusing in Backscattering Mode", Scientific Reports, 2014, pp. 1-7, vol. 4, No. 7156.

Suzuki, Y., et al., "Continuous scanning of a time-reversed ultrasonically encoded optical focus by reflection-mode digital phase conjugation", Optics Letters, Jun. 15, 2014, pp. 3441-3444, vol. 39, No. 12.

Liu, Y., et al., "Time-reversed ultrasonically encoded optical focusing through highly scattering ex vivo human cataractous lenses", Journal of Biomedical Optics, Jan. 2018, p. 010501-1-010501-4, vol. 23, No. 1.

* cited by examiner

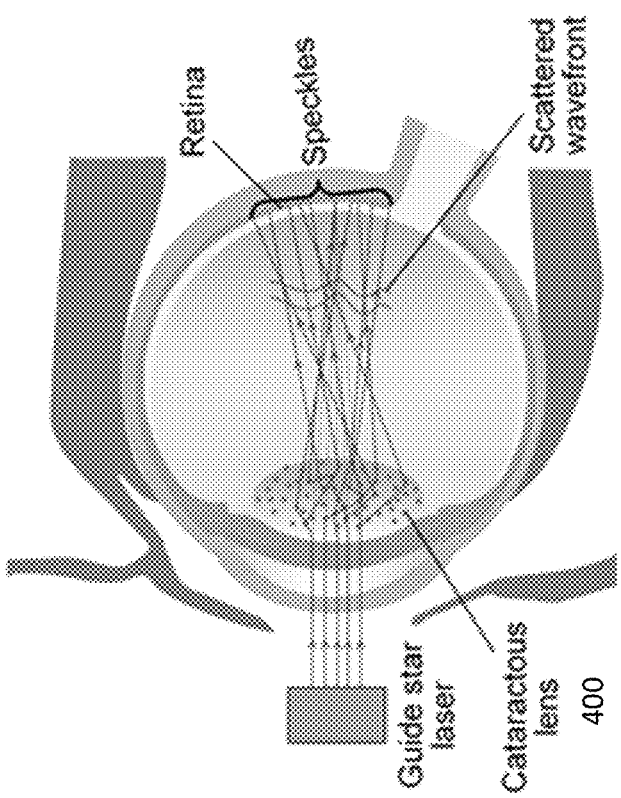
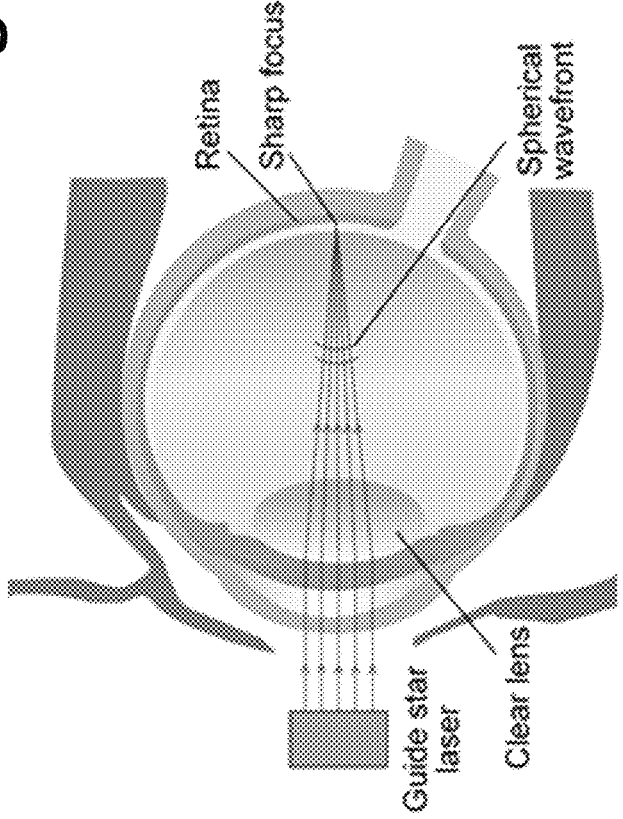
Fig. 4A
Fig. 4B

FOCUSING LIGHT THROUGH CATARACTOUS LENSES

CROSS REFERENCE TO RELATED APPLICATIONS

This application claims the benefit under 35 U.S.C. Section 119(e) of commonly-assigned U.S. Provisional Patent Application Ser. No. 62/580,339, filed on Nov. 1, 2017, entitled "FOCUSING LIGHT THROUGH CATARACTOUS LENSES," by Lihong Wang, Frank Brodie, Yuecheng Shen, Changhuei Yang, Yan Liu, and Haowen Ruan, (CIT-7894-P); and which application is incorporated by reference herein.

STATEMENT REGARDING FEDERALLY SPONSORED RESEARCH AND DEVELOPMENT

This invention was made with government support under Grant No(s). EB016986 & CA186567 & NS090577 awarded by the National Institutes of Health. The government has certain rights in the invention.

BACKGROUND OF THE INVENTION

1. Field of the Invention

This invention relates to a method and system for imaging and focusing electromagnetic radiation in a scattering medium.

2. Description of the Related Art (Note: This application references a number of different publications or references as indicated throughout the specification by one or more reference numbers as superscripts, e.g., [x]. A list of these different publications or references ordered according to these reference numbers can be found below in the section entitled "References." Each of these publications or references is incorporated by reference herein.)

Normal development of the visual pathways in the central nervous system relies on clear images being projected on the retina throughout the first year of life. Disruption of this can lead to the development of amblyopia—a condition in which individuals, despite having structurally normal eyes, have intractable poor vision due to the underdevelopment of the cortical visual system[1-3].

A cataract is a clouding of the normally transparent crystalline lens in the eye, and it scatters light coming toward a retina. Cataracts cause half of blindness and 33% of visual impairment worldwide. Congenital cataracts occur approximately one in every 2500 live births[4]. Since no clear images are projected to the retinas of the infants with such a disease, early diagnosis and treatment of congenital cataract is critical for the prevention of amblyopia[5, 6].

Currently, the standard of care is to perform cataract removal surgery within the first month of life[5, 6], to minimize the effects of cataract on the normal development of the visual pathways. The infant is usually left aphakic, i.e., without a physiological lens in the eye, and it relies on a contact lens. Unfortunately, a common complication of cataract extraction is the development of glaucoma (termed aphakic glaucoma, which involves damaging of the optic nerve that leads to vision loss). While the precise mechanism for this complication is not well understood, it has been shown that earlier surgery leads to an increased risk[7-9]. Aphakic glaucoma is a devastating complication with significant irreversible visual loss at a very young age. Frequently it requires additional surgeries and multiple medications.

Ultimately, current management of congenital cataract puts the doctor in a difficult position: the cataract needs to be removed promptly to prevent amblyopia, but the surgeon knows that aphakic glaucoma could lead to equally profound vision loss after the cataractous lens is removed. Although the risk of aphakic glaucoma can be reduced eight-fold by delaying the surgery until four months of life, evidence shows that this delay would lead to more severe amblyopia[5-7].

What is needed then, are improved methods of treating amblyopia. The present disclosure satisfies this need.

SUMMARY OF THE INVENTION

The present disclosure describes a device for irradiating ocular tissue.

The device can be embodied in many ways including, but not limited to, the following.

1. The device comprising a source of electromagnetic radiation; a beacon scattering the electromagnetic radiation transmitted through an opacity in ocular tissue so as to form scattered electromagnetic radiation; and a modulator transmitting output electromagnetic radiation having a field determined from a recording of the scattered electromagnetic radiation transmitted through the opacity, so that the output electromagnetic radiation is transmitted through the opacity to the beacon.

2. The device of embodiment 1, wherein the ocular tissue comprises lens tissue comprising cataractous tissue or other light scattering media in the optical axis of an eye.

3. The device of one or any combination of embodiments 1-2, wherein the beacon is positioned on retinal tissue.

4. The device of one or any combination of the previous embodiments 1-3 further comprising a transmitter of ultrasound positioned so as to transmit ultrasound forming the beacon including a focus of the ultrasound, wherein the ultrasound frequency shifts the electromagnetic radiation transmitted through the opacity so as to form the scattered electromagnetic radiation comprising frequency shifted electromagnetic radiation.

5. The device of one or any combination of the previous embodiments 1-4, wherein the output electromagnetic radiation comprises a phase conjugate of the scattered electromagnetic radiation transmitted through the opacity.

6. The device of one or any combination of the previous embodiments 1-5, further comprising a detector outputting a signal comprising the recording in response to the scattered electromagnetic radiation received on the detector; and a computer connected to the detector and the modulator. The computer determines a phase, an amplitude, or an amplitude and a phase of the output electromagnetic radiation from the recording; and the modulator modulates the output electromagnetic radiation so that the output electromagnetic radiation has the phase, the amplitude, or the amplitude and the phase.

7. The device of embodiment 6, wherein the detector comprises a wavefront sensor measuring a wavefront for each spatial location in the scattered electromagnetic radiation associated with a stimulation pattern; the computer synthesizes an output wavefront of the output electromagnetic radiation using the wavefront; and the modulator modulates the output electromagnetic radiation so as to transmit the stimulation pattern to the beacon.

8. The device of one or any combination of the previous embodiments 6-7, wherein the modulator comprises pixels that are sequentially modulated so as to scan the output electromagnetic radiation representing different points in the stimulation pattern across retinal tissue within a duration of persistence of vision so that a subject perceives the stimulation pattern, wherein the beacon is on the retinal tissue, and/or the computer uses an optical memory effect to determine the output wavefronts for neighboring points in the stimulation pattern by adding different phase gradients so as to reduce a number of the wavefronts measured by the wavefront sensor.

9. The device of one or any combination of the previous embodiments 6-8, wherein the modulator comprises pixels, wherein the pixels have variable transmissivity, reflectivity, or emission so as to modulate an intensity of the output electromagnetic radiation transmitted from the pixels, the computer controls the transmissivity, reflectivity, or emission of each of the pixels so as to form a varying intensity comprising a stimulating pattern capable of stimulating nerves on retinal tissue, and the beacon is on the retinal tissue.

10. The device of one or any combination of the previous embodiments 6-9, wherein the computer determines, from the signal, values representing a phase, an amplitude, or a phase and an amplitude of the scattered electromagnetic radiation at spatial locations associated with the stimulating pattern; and the computer determines the phase, an amplitude, or the amplitude and the phase of the output electromagnetic radiation from the values.

11. The device of one or any combination of the previous embodiments 7-10, wherein the stimulating pattern comprises a line.

12. The device of embodiment 11, wherein the stimulating pattern comprises a pair of lines moving closer together so as to measure visual acuity.

13. The device of one or any combination of embodiments 7-12, wherein the computer temporally controls the transmissivity, reflectivity, or emission of each of the pixels so that all points or regions of the stimulating pattern are transmitted from the modulator sequentially in time, e.g., within a duration of 50 milliseconds or within a duration of a persistence of vision of an infant.

14. The device of one or any combination of embodiments 7-13, wherein the computer determines, from the signal, values representing a phase, an amplitude, or a phase and an amplitude of the scattered electromagnetic radiation for a subset of spatial locations associated with the stimulating pattern; and the computer uses an optical memory effect to calculate the phase and/or amplitude for neighboring points in the stimulating pattern by adding different phase gradients.

The present disclosure describes how embodiments of the apparatus and methods described herein can be used for focusing light noninvasively through highly scattering cataractous lenses and so as to stimulate the retina, thereby preventing amblyopia. This approach allows cataractous lens removal surgery to be delayed and hence greatly reduces the risk of complications from early surgery. As illustrated herein, embodiments of the device employ a wavefront shaping technique named time-reversed ultrasonically encoded (TRUE) optical focusing in reflection mode, so as to focus (e.g., 532 nm) light through a highly scattering human cataractous lens.

Variations of the wavefront sensing technique have other clinical applications as described herein. For example, other embodiments described herein in include a device for irradiating ocular tissue, comprising a source of electromagnetic radiation; a beacon scattering the electromagnetic radiation transmitted through ocular tissue so as to form scattered electromagnetic radiation; a wavefront sensor measuring a phase and/or amplitude of the scattered electromagnetic radiation transmitted through the opacity; and a computer mapping optical properties at different spatial locations across the ocular tissue using the phase and/or amplitude. In one or more examples, the optical properties are used to inform a machine (e.g., including a laser) on how to ablate the cornea to correct for optical aberrations caused by the corneal or lens tissue (e.g., on how to ablate the cornea for optical clarity).

BRIEF DESCRIPTION OF THE DRAWINGS

Referring now to the drawings in which like reference numbers represent corresponding parts throughout:

FIG. 1A illustrates the lens is so scattering that the "CALTECH" characters underneath cannot be observed. FIG. 1B is a schematic of the setup to measure the extinction coefficient of the cataractous lens. M, mirror; PD, photodetector.

FIG. 3A shows a portion of the phase map displayed on the SLM to achieve TRUE focusing. FIG. 3B is a histogram of the phase map. FIG. 3C is an image of the TRUE focus observed on camera CAM2. FIG. 3D shows no focus was observed when we shifted the phase map displayed on the SLM horizontally by 10 pixels to break the time-reversal symmetry. Scale bar, 100 μm.

FIGS. 4A-4B. Illustration of why the traditional method to generate a guide star does not work. FIG. 4A shows that for a clear eye, a guide star can be directly formed onto the retina by sending in a plane wave. FIG. 4B shows that for an eye with a cataract, light is scattered within the cataract. As the light projected onto the retina is scrambled, no traditional guide star can be formed.

FIG. 5A shows light is projected through the cataractous lens and is diffusely scattered due to the heterogeneous refractive index within the cataract. FIG.

5B shows an ultrasonic focus can be formed at the targeted position because biological tissue is essentially transparent to ultrasound. FIG. 5C illustrates encoding diffused coherent light via a focused ultrasonic wave, which provides an internal guide star. The wavefront of the tagged light is filtered and measured using heterodyne holography. FIG. 5D shows the conjugate wavefront of the tagged light is time-reversed back to the ulrasonic focus, yielding a TRUE focus.

DETAILED DESCRIPTION OF THE INVENTION

Figures 1A, 1B:
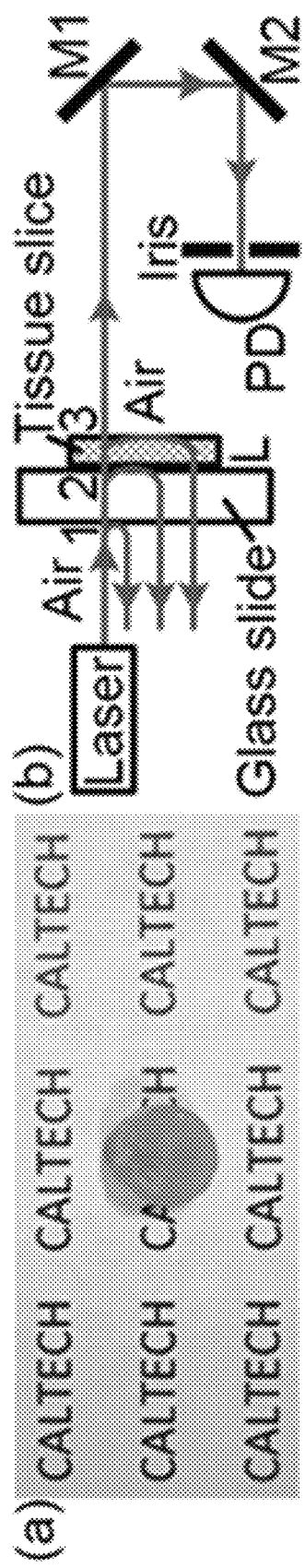
FIGS. 1A-1B Illustration of the turbidity of an ex vivo human cataractous lens.

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Technical Description

First Example

One or more embodiments of the present invention comprise a system and method capable of focusing light through the opaque cataractous lens to stimulate the retina, thereby preventing amblyopia and giving the eye more time to mature (particularly the eye's drainage system, since glaucoma occurs with increased intraocular pressure). This approach allows cataractous lens removal surgery to be delayed and thereby greatly reduces the risk of aphakic glaucoma[7].

The technique of focusing light through opaque cataractous lenses for retina stimulation uses wavefront shaping. Wavefront shaping includes a class of methods that employ scattered photons for focusing light through highly scattering media such as biological tissue[10-13]. These methods work by shaping the wavefront of an incident light field, so that the scattered light can constructively interfere at locations of interest to form optical foci[14]. Three types of wavefront shaping techniques have been developed, including feedback-based wavefront shaping[14, 15], transmission matrix measurement[16, 17], and optical phase conjugation (OPC)/time reversal[18-21]. Among them, OPC achieves the highest focusing speed for a given number of wavefront sensing and control elements (runtime <10 ms for >10[5] elements[22-24]), by determining the required wavefront globally instead of stepwise[25]. This feature makes OPC most promising for in vivo applications where speckles decorrelate fast due to physiological motions[22, 26].

OPC focuses light inside scattering media by first measuring and then phase conjugating (time reversing) the scattered light field emitted from a guide star[11], which is positioned at a targeted focusing location deep inside a scattering medium. In embodiments illustrated herein, focused ultrasound is used to noninvasively provide a (virtual) guide star[27-29], which is freely addressable within tissue. Due to the acousto-optic effect, a portion of the light passing through the ultrasonic focus changes its frequency by an amount equal to the ultrasonic frequency. These so-called ultrasound-tagged photons emitted from the virtual guide star (ultrasonic focus) are then scattered as they propagate through the turbid medium toward a camera. By measuring the wavefront of the ultrasound-tagged light and then performing OPC, a phase-conjugate version of the ultrasound-tagged light is generated. The phase-conjugate version partially retraces the original trajectory back through the scattering medium and converges to the ultrasonic focus (the source of the ultrasound-tagged light) as if time has been reversed. This focusing technique based on ultrasound-guided optical phase conjugation is known as time-reversed ultrasonically encoded (TRUE) optical focusing[27-29].

1. Example Cataractous Lens

In this example, a cataractous lens was harvested from a 68-year-old male donor at University of California San Francisco (UCSF) Medical Center. An illustration of the cataractous lens 100 is shown in FIG. 1A. Because of the strong scattering of light in the lens, the "CALTECH" characters cannot be observed underneath the lens. The transmission of collimated ballistic light through a tissue slice (attached to a glass slide [FIG. 1B]) was measured to quantify the extinction coefficient $\mu_t$ of the cataractous lens. Rather than using the whole lens, a thin tissue slice (thickness L=100 μm, cut with a vibratome) was used to reduce the number of scattered photons[30]. To reject the scattered light, the distance between the sample and a photodetector was kept long (2.6 m), and an iris with a diameter of 1.5 mm was used. According to Beer's law, the transmitted light power received by the photodetector $P_1 = P_0 t_1 t_2 \exp(-\mu_t L) t_3$, where $P_0$ is the incident light power on the glass slide, $t_1$, $t_2$, and $t_3$ are the transmission coefficients of the air-glass, glass-tissue, and tissue-air interfaces, respectively [FIG. 1B]. The transmitted light power $P_2$ through another tissue slice with a thickness of 2 L was measured do reduce the unknown variables by normalization. Since $P_2=P_0 t_1 t_2 \exp(-\mu_t 2L)t_3$, $\mu_t=\ln(P_1/P_2)/L=32\pm4$ mm$^{-1}$. The light was focused through a 3.5 mm thickness of cataractous lens (equal to 112 mean free paths).

2. Example Apparatus

Figure 2:
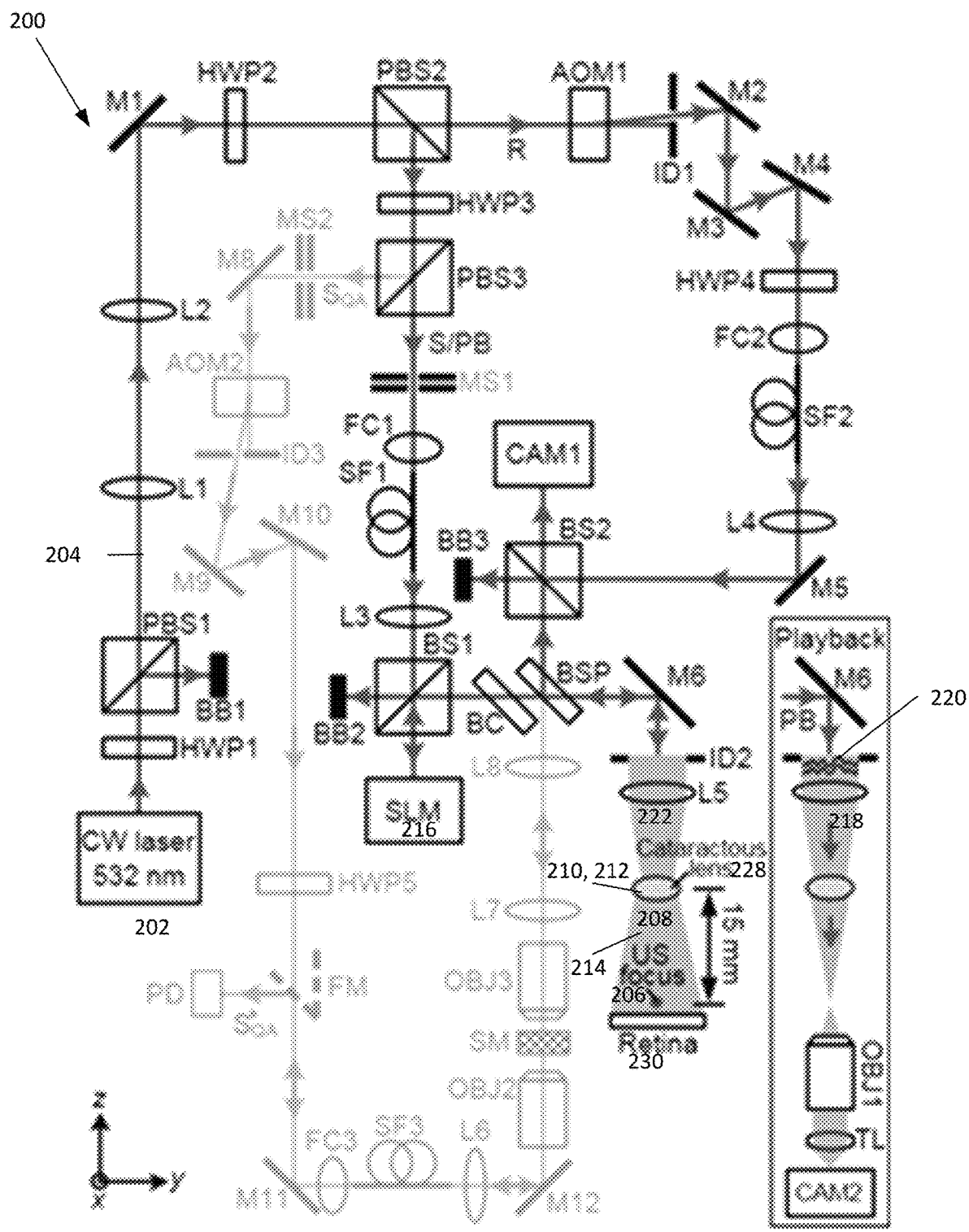
FIG. 2 Schematic of the set-up for focusing light through ex vivo human cataractous lens, according to one or more embodiments of the present invention. The optical path in light green was used for assessing and assuring the performance of the OPC set-up on a daily basis. The inset shows the schematic of the setup for observing the TRUE focus. AOM, acousto-optic modulator; BB, beam block; BC, beam compensator; BS, cube beamsplitter; BSP, plate beamsplitter; CAM, camera; CW, continuous-wave; FC, fiber coupler; FM, flip mirror; HWP, half-wave plate; ID, iris diaphragm; L, lens; M, mirror; MS, mechanical shutter; OBJ, objective; PB, playback beam; PBS, polarizing beamsplitter; PD, photodiode; R, reference beam; S, sample beam; SF, polarization-maintaining single-mode optical fiber; SQA, sample beam for quality assurance of the OPC system; S*$_{QA}$, conjugate of S$_{QA}$. SLM, spatial light modulator; SM, scattering medium (two layers of tapes); TL, tube lens; US, ultrasound.

FIG. 2 illustrates the reflection-mode TRUE focusing system[31] used to focus light through the human cataractous lens (lens comprising a cataract or opacity) according to one or more examples using the lens tissue described in section 1. The phase map of the ultrasound-tagged light field was measured using heterodyne holography[21, 29, 32-34] and the ultrasound-tagged light field was phase conjugated by displaying the conjugate phase map on a spatial light modulator (SLM) that modulated the phase of light. Following time reversal, the phase conjugated light converged to the ultrasonic focus, thus forming an optical focus.

To stimulate the retina, the ultrasonic focus is placed either on (or sufficiently close to) the retina. In the example illustrated in FIG. 2, the ultrasound focus was positioned close to the retina so that the scattering retina could be removed to directly image the optical focus by an imaging system (comprising objective OBJ1, tube lens TL, and camera CAM2, see FIG. 2 inset) and verify functioning of the TRUE focus. The distance between the lens and the ultrasonic focus was 15 mm, which is the distance between the lens and the retina of an infant.

FIG. 2 illustrates the output of a 200 mW, 532 nm continuous-wave laser (Excelsior-532-200, Spectra-Physics) was split into a sample beam (S)/playback beam (PB) and a reference beam (R). Both beams were spatially filtered by single-mode fibers and collimated. The frequency of R was up-shifted by 50 MHz+10 Hz by acousto-optic modulator AOM1 before R was reflected to scientific CMOS camera CAM1 (pco-edge 5.5, PCO) by beamsplitter BS2. In the other arm, S/PB beam reflected from the SLM (Pluto, Holoeye) and mirror M6 illuminated the cataractous lens, with an intensity of 15 mW/cm$^2$. A portion of the light back-scattered from a cow retina was tagged by a 50 MHz focused ultrasonic field, collected by lens L5, and then reflected to camera CAM1 by plate beam splitter BSP (50T/50R). On CAM1, the ultrasound-tagged light interfered with reference beam R, with a beat frequency of 10 Hz. Triggering the camera at four times the beat frequency (40 Hz) and recording successive interferograms ($I_0$, $I_{\pi/2}$, $I_\pi$, $I_{3\pi/2}$) enabled reconstruction of the phase map of the ultrasound-tagged light $\varphi=\mathrm{Arg}[I_0-I_\pi)+i(I_{\pi/2}-I_{3\pi/2})]$, where Arg [z] computes the principal value of the argument of complex number z. To achieve optical phase conjugation, the conjugate phase map of $\varphi$ was displayed on the SLM (positioned at the mirrored position of the camera sensor relative to beamsplitter BSP). The wavefront-shaped light then converges to the ultrasonic focus after passing through the cataractous lens (FIG. 2 inset). An iterative TRUE focusing scheme[31, 35, 36] was used to increase the ultrasound-tagged light signal and resolution, by repeating the TRUE focusing procedure using a previously established TRUE focus. Eight iterations were employed.

Figure 3A:
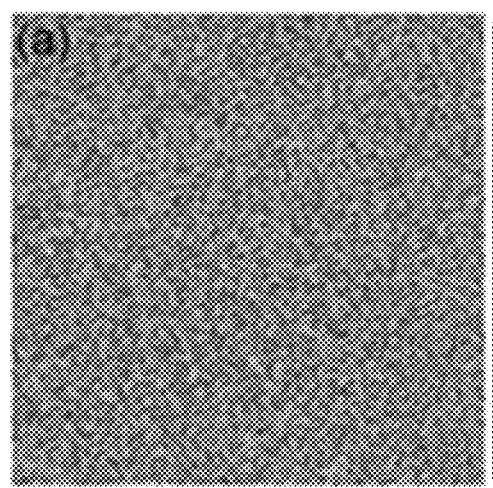
FIG. 3A-3D Focusing light through ex vivo human cataractous lens according to one or more embodiments of the present invention.
Figure 3B:
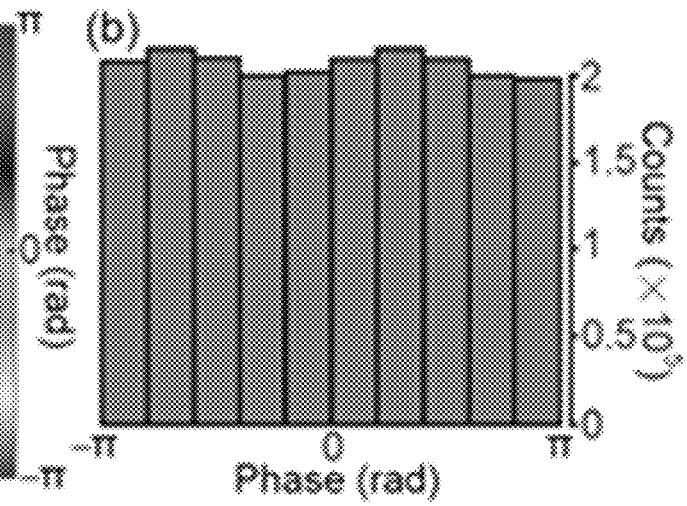

FIG. 3A shows a portion of the phase map displayed on the SLM to achieve TRUE focusing. Only the central 200×200 pixels out of 1920×1080 pixels are shown due to space constraint. The histogram of the whole phase map shows that the phase values are nearly uniformly distributed between 0 to 2π [FIG. 3B], following the statistics of a fully developed speckle. FIGS. 3A and 3B show that the wavefront observed here is much more complex than that in traditional adaptive optics. This capability to tackle complex wavefront associated with highly scattering media is enabled by a reliable guide star, and the large pixel counts (>10$^6$ pixels) of both the wavefront sensor (scientific CMOS camera) and the wavefront modulator (SLM) used in the technique illustrated here.

Figure 3C:
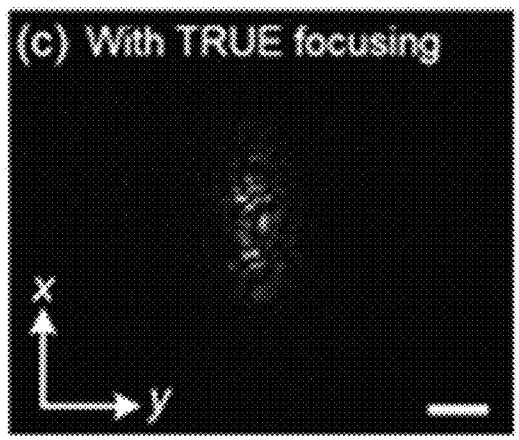
Figure 3D:
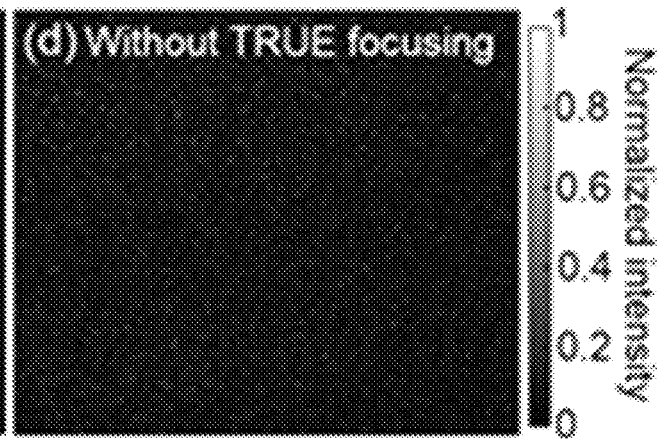

When the phase map shown in FIG. 3A was displayed on the SLM, the wavefront-shaped light was focused through the cataractous lens, and the optical focus observed on camera CAM2 is shown in FIG. 3C. The full width at half maximum focal spot size is 50 μm along the y-direction, and 172 μm along the x-direction, which is the acoustic axis direction. The average intensity inside the focus is 13 times higher than the average intensity of the surrounding background. In a control experiment, the phase map displayed on the SLM was shifted horizontally by 10 pixels to break the time-reversal symmetry, and no focus was observed [FIG. 3D], demonstrating proper functioning of the technique.

3. Applicability to In Vivo Tissue

Focusing light inside scattering media using wavefront shaping is an area of active research, because it breaks the optical diffusion limit[37, 38] and promises to revolutionize biophotonics by enabling noninvasive deep-tissue optical imaging, manipulation, and therapy. Recently, 532 nm light was successfully focused through 25 mm thick ex vivo chicken tissue, as well as through 96 mm thick tissue-mimicking phantoms[21], demonstrating the applicability of OPC based wavefront shaping for biomedicine. For in vivo applications, the system runtime should be shorter than the speckle correlation time associated with living tissue, which is on the order of 1 ms, due to blood flow[22, 26, 39]. High-speed systems[22-24, 33, 40, 41] with a reduced number of controls can be adapted for in vivo deep-tissue applications. In contrast, since there are no blood vessels in human lens or in retina layers at the fovea and the cataractous lens can be static for hundreds of milliseconds, the speckle correlation time is much longer for human lenses. Therefore, focusing light through human cataractous lens in vivo can be achieved using the wavefront shaping techniques described herein.

The quantity of visual stimulation needed to prevent amblyopia has been addressed by the Mitchell laboratory's studies in cats. They found that only 30 minutes of visual experience per day during the critical period allows for the development of normal acuity when kittens are binocularly deprived for the remaining 23.5 hrs/day by being kept in darkness.[36] A similarly brief period of daily binocular vision is sufficient to avert the effects of even very prolonged periods (7 hrs/day) of monocular vision—comparable to the entire waking period—as assessed either by behavioral measurements of acuity[37] or by measurements of visual cortical responses.[38] The same brief amount of daily binocular visual experience, less than one hour, was required for the normal development of functional ocular dominance domains in the primary visual cortex no matter how long the period of monocular vision[39], and acuity developed largely albeit incompletely with such brief exposures. The development of full normal acuity, equal to that in the fellow eye, required longer periods of binocular exposure, up to 30% of waking hours. Findings from other laboratories are consistent with these reports.

The most extensive primate studies on the quantity of visual experience necessary to prevent amblyopia have come from the Smith and Chino laboratories. Behavioral measurements of contrast sensitivity in Macaque monkeys reared with simulated cataracts (produced by a diffusing lens over one eye) showed that, as expected, continuous monocular form deprivation caused severe amblyopia. However, one hour of unrestricted vision reduced the degree of amblyopia by 65% and two hours/day reduced the deficit by 90%.[19] Recordings from neurons in the primary visual cortex of macaque monkeys demonstrated that one hour per day of binocular vision in animals otherwise seeing only monocularly largely preserved normal visual responses, and two hours per day led to a result nearly indistinguishable from normal.[40] Findings using other measures of visual development[4,21] and findings in other species reviewed in Espinosa and Stryker (2012)[20] are consistent with the more extensive results noted above.

A number of studies indicate that, as in adult plasticity, the most salient factor is the degree to which the stimulation is effective in driving neurons in the visual cortex. For example, in cats see Stryker, M. P., Sherk, H., Leventhal, A. G., and Hirsch, H. V. (1978);[41] in rodents, see FIGS. 6 and 7 in Kaneko, M., Fu Y., and Stryker, M. P. (2017).[32] Diffuse light stimulation is nearly ineffective, and the most effective stimuli are bars or edges moving across the visual field, with different cells in different columns driven by different orientations. The example stimuli that can be created using TRUE technology described herein can be used for this purpose.

II. Second Example

In Vivo Application

1. Introduction

Imaging through a cataract poses a unique challenge that traditional adaptive optics cannot overcome: the inability to clearly project a guide star beyond the media opacity. Traditional optical guide stars require relatively sharp projection, which can only be accomplished through low scattering media (such as the atmosphere or a normal eye FIG. 4A) and cannot be achieved through a highly scattering medium (in our case, the cataract 400, FIG. 4B). The light from a laser is scattered within the cataract before reaching the retina. As a result, a speckle pattern of randomly distributed bright spots is formed on the retina. The observer would be unable to differentiate between all the light rays reflected back from many bright spots on the retina and consequently unable to calibrate the adaptive optics system.

FIGS. 5A-5D illustrates how TRUE optical focusing according to one or more embodiments described herein overcomes this limitation by ultrasonically "tagging" light once it has passed through the cataract, creating a guide star. As biological tissue is nearly ultrasonically transparent, an ultrasonic beam cis well focused on the retina to modulate light reaching the focus through ultrasonically induced scatterer displacement and refractive index variation, akin to the Doppler shift. This tagged light is then reflected off the retina and undergoes distortion by the cataract a second time before being seen by the observer. By identifying the "tagged" light, the observer only records light that has reached the ultrasonic focus, which serves as a guide star. The tagged light is time-reversed back onto the retina at the original ultrasonic focus with a high contrast. The focal point can then be scanned to form a high-contrast line or grating pattern.

Figure 5A:
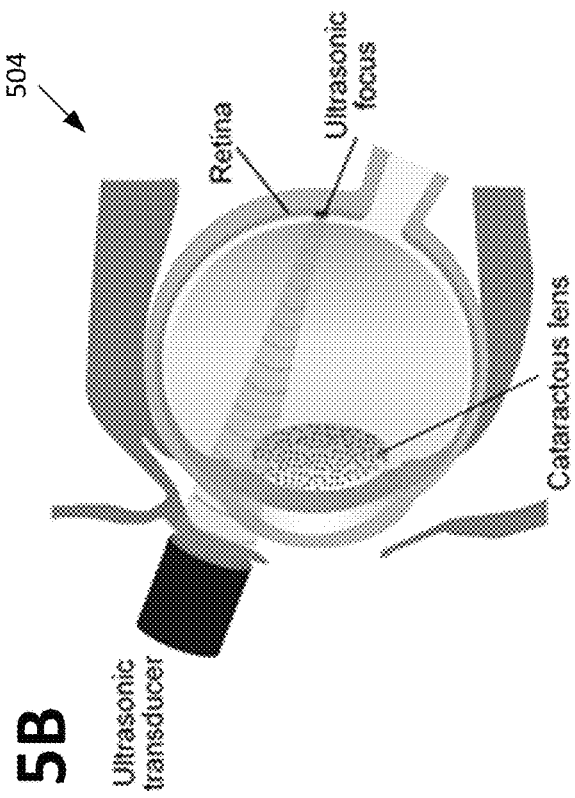
FIGS. 5A-5D. Principle of time-reversed ultrasonically encoded (TRUE) optical focusing deep inside or through scattering media according to one or more embodiments of the present invention.
Figure 5B:
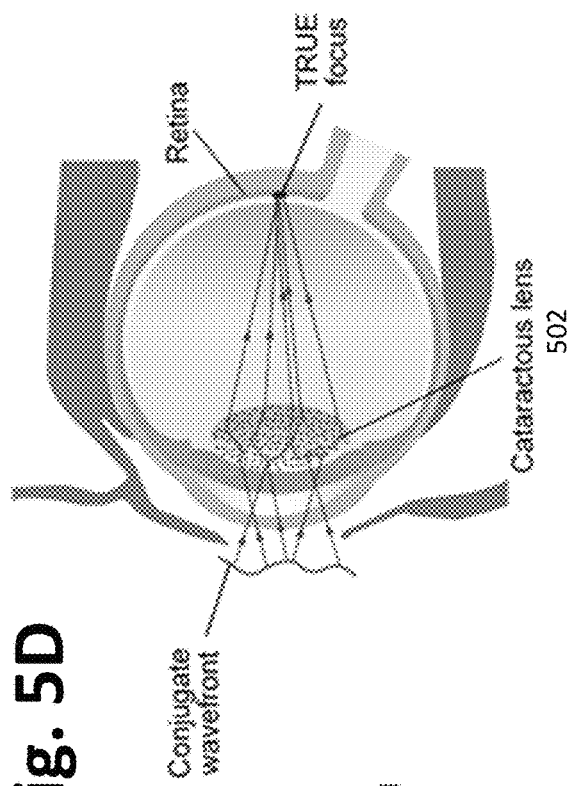
Figure 5C:
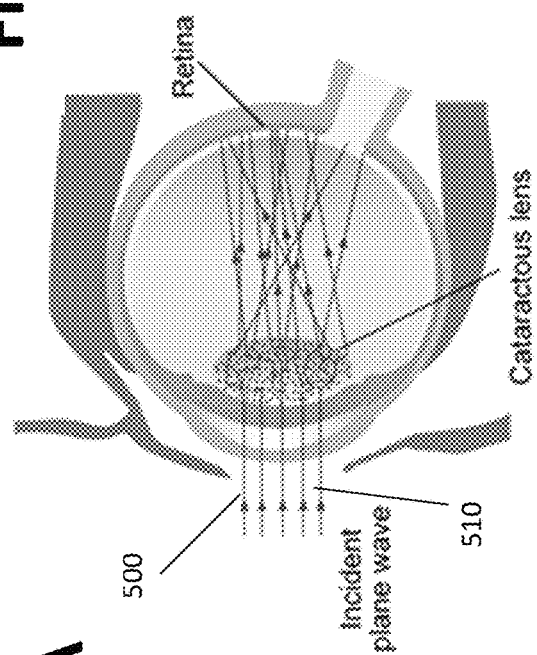
Figure 5D:
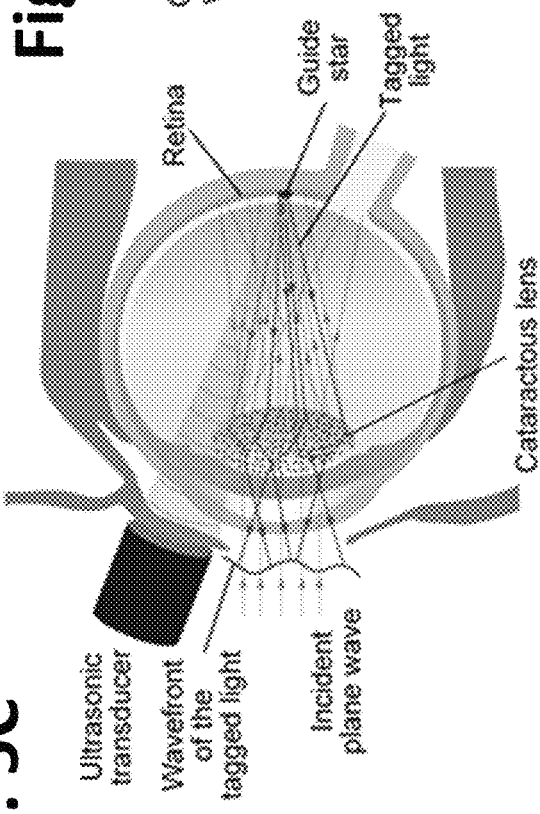

FIGS. 5A-5D also shows the working principle of TRUE focusing. (1) Light is projected into the scattering medium and diffusely scattered due to the heterogeneous refractive index within the cataract 500. The optical paths of photons are illustrated using green lines 502 (FIG. 5A). (2) Since the scattering medium is ultrasonically transparent, we can directly form an ultrasonic focus at the targeted position inside the scattering medium (FIG. 5B). (3) The ultrasonic focus serves as an internal guide star. Due to the light-sound interactions in the medium, a portion of light passing through the ultrasonic focus is frequency shifted. The amount of the frequency shift is equivalent to the central frequency of the ultrasonic wave. These frequency-shifted photons, represented with red lines, are now "ultrasonically tagged" (FIG. 5C)). To isolate these tagged photons from a large number of untagged photons, we apply heterodyne holography by introducing a reference beam. The reference beam forms holographic images with the tagged photons, and these holographic images are captured by a camera. The camera then transfers these images to a computer for analysis. In the computer, the wavefront of these tagged photons is calculated (FIG. 5C). (4) The conjugate wavefront of the tagged photons is sent to a spatial light modulator (SLM) for display. A reading beam with a planar wavefront acquires this conjugated wavefront from the SLM. Due to the time-reversal principle, light with this conjugated wavefront traces the original optical paths back to the position of the ultrasonic focus, as if time evolves backwards (FIG. 5D)). In this way, we can form an optical focus deep inside the scattering medium. The formed optical focus by TRUE technology has the same dimensions as the ultrasonic focal dimensions and is unaffected by multiple scattering of light. Thus, by compensating for the optical scattering effect using the ultrasonically encoded guide star, sharp, high-contrast images can be projected through the cataract onto the retina.

2. TRUE Processing Speed According to One or More Examples

Nearly instantaneous processing can be used to render images in real time and account for microsaccades, respiration and other movements. In conventional systems, ultrasound-guided DOPC has been limited by the low speeds of cameras, data transfer, data processing, and SLMs. The low speeds prevent DOPC from being applied to thick living biological tissue, because the motion of the scattering elements inside tissue causes the speckles to decorrelate and breaks the time reversal symmetry, ultimately preventing a formed image from being projected. By employing the state-of-the art ferroelectric liquid crystal based SLM and a novel double-shot binary-phase modulation scheme, the world's fastest TRUE system has a system runtime of 7.0 ms.[24] The demonstrated runtime to focus light into a scattering medium is up to two orders of magnitude shorter than those of previous wavefront shaping systems.

3. Apparatuses According to One or More Embodiments

Figure 6A:
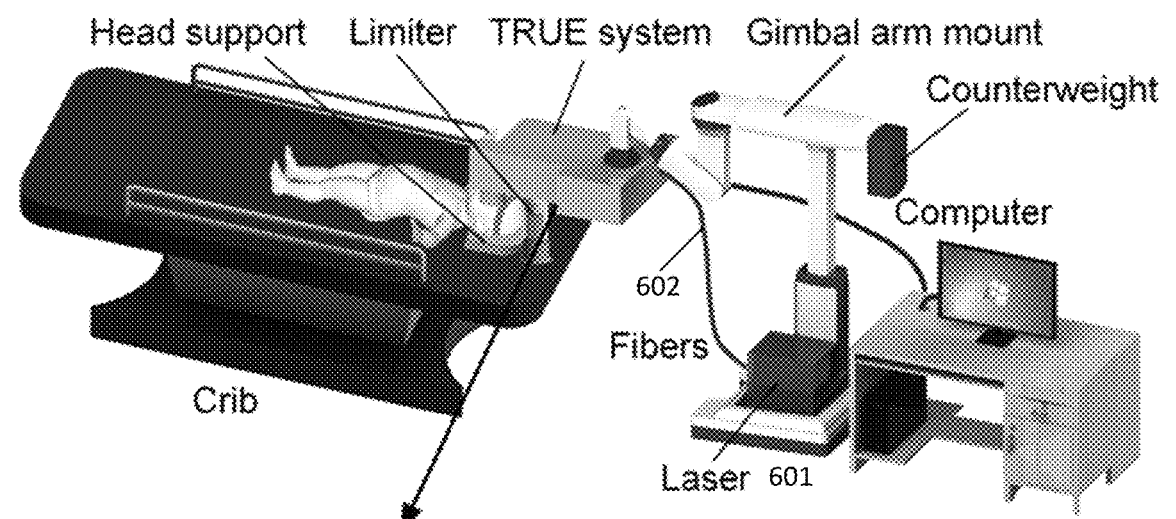
FIG. 6A. System overview according to one or more embodiments of the present invention.
Figure 7:
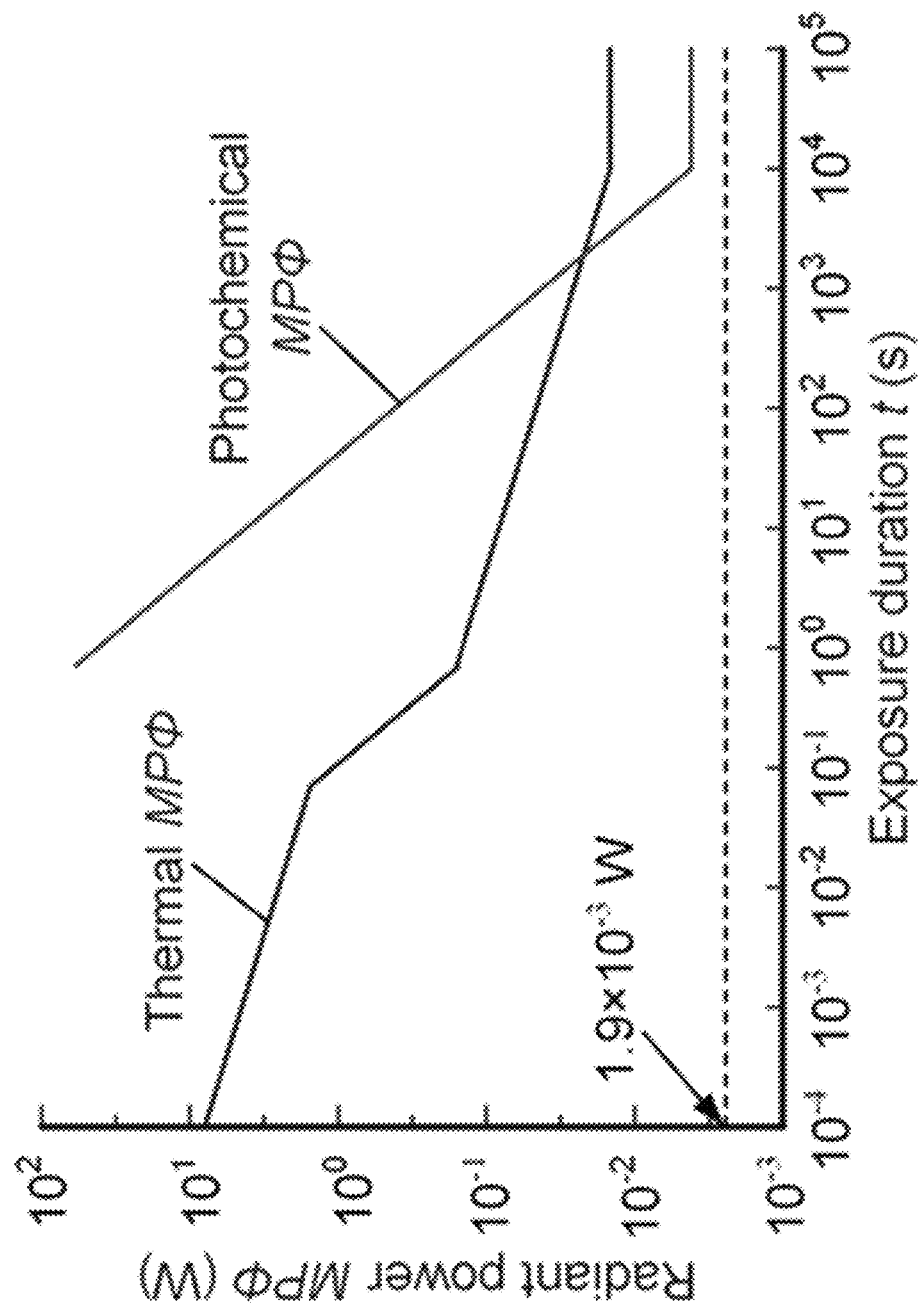
FIG. 7 Radiant power MPΦ as a function of exposure duration t for λ=532 nm that can be used in one or more embodiments of the present invention.
Figure 8:
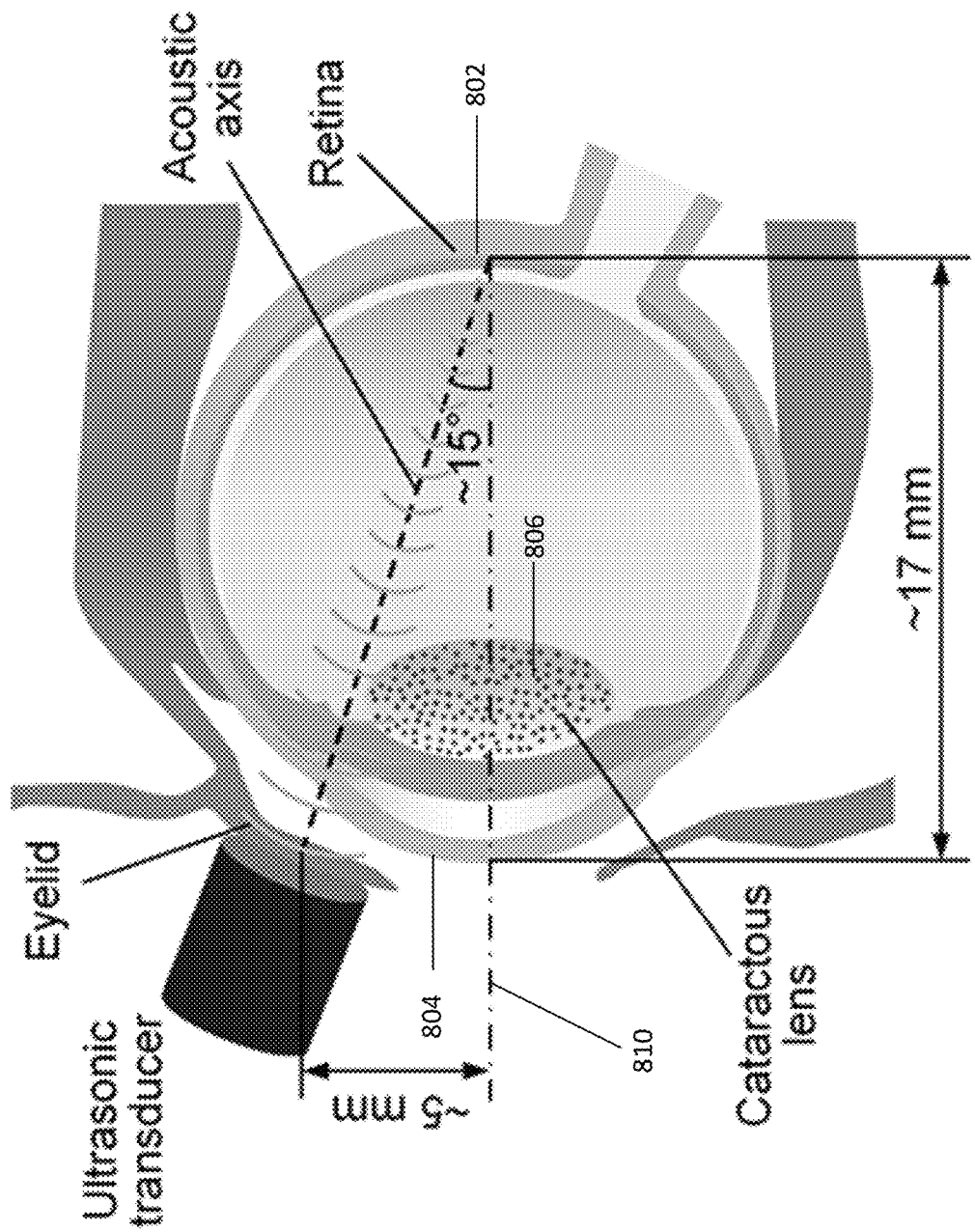
FIG. 8. Anatomy of an infant eye coupled to ultrasonic transducer according to one or more embodiments of the present invention.

FIG. 6A illustrates a novel TRUE system for use on patients according to one or more examples of the present invention. The system can be packaged into a sealed enclosure. The system includes a heavy-duty gimbal, adjustable for translational and rotational movements. In one or more embodiments wherein the gimbal is integrated with the enclosure, a heavy metal mass is mounted on the other end of the gimbal arm to counter balance the weight of the enclosure. The optical fibers for light delivery and the electronic cables for control signals are connected to a laser and a computer, respectively.

During treatment, the infant lies supine on the crib with the head held steadily by a head support. In embodiments using a light source with a narrow bandwidth, there is the option to leave the ambient light on or switch it off. The infant eye remains open during the treatment so that light can be projected into the eye.

In one or more examples, to minimize irradiance (mW/cm²) while avoiding irradiating the iris, the laser beam is broadened to ~3 mm in diameter, which fills approximately half of the mydriatic pupil (5-6 mm in diameter). In one or more examples, to protect the infant's head, a limiter with an adjustable height is installed on one side of the bed to support the enclosure. The limiter prevents the enclosure from falling on the infant.

Figure 6B:
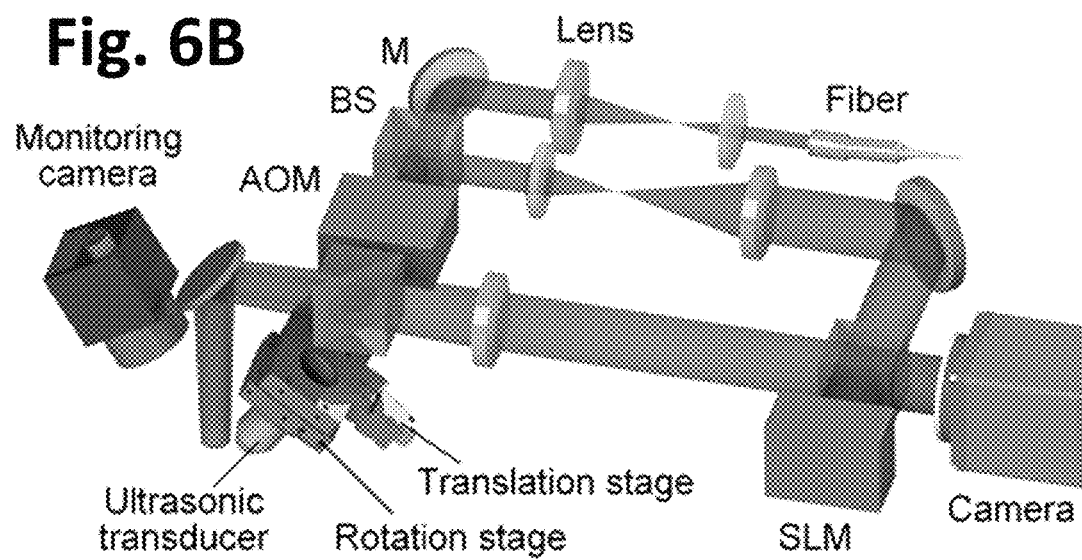
FIG. 6B. Detailed layout of the key components inside the enclosure according to one or more embodiments of the present invention. AOM, acousto-optic modulator, BS, beamsplitter, M mirror, SLM spatial light modulator.

FIG. 6B illustrates an example detailed layout of the key components inside the enclosure according to one or more embodiments. A single-mode optical fiber outputs (e.g., 532-nm green) light. The light beam is expanded by a pair of lenses and split into a reference beam and a probing beam. The probing beam is sent to the patient's eye, where it is scattered by the cataractous lens. A high-frequency focused ultrasonic transducer, custom-made with a large aperture, is used to provide a TRUE guide star. The ultrasonic transducer stays in contact with the infant's eyelid through ultrasonic coupling gel during treatment. When the ultrasonic transducer is turned on, an ultrasonic wave is focused on the front surface of the retina. The ultrasonic transducer is mounted on motorized stages for raster scanning and rotation. The 532 nm light passes through the pupil along the visual axis. Once the light is ultrasonically tagged, a portion of the frequency-shifted light is reflected back to the TRUE system and enter the DOPC module, which is composed of a camera and an SLM. The DOPC module measures the scattered wavefront of the tagged light and performs optical time reversal/OPC, resulting in an optical focus on the patient's retina.

In one or more examples, to generate a line, the optical focus is scanned within the duration of the persistence of vision. In one or more examples, to support two-dimensional (2D) fast scanning and rotation of the ultrasonic transducer, the transducer is mounted on two motorized linear stages (e.g., Physik Instrumente, PI V-528) and one motorized rotation stage (e.g., Physik Instrumente, A-627.075). In the example, the linear stage has a travel range of 20 mm, a resolution of 20 nm, and a maximum velocity of 250 mm/s; the rotational mount has a travel range of >360° with an accuracy as fine as 8 μrad; and a monitoring camera is also installed to surveil the condition of the human eye, helping physicians to align the system.

4. Sources of Electromagnetic Radiation (e.g., Laser) According to One or More Embodiments In one or more embodiments, the maximum light intensity on the retina is no greater than 9.5 mW/cm² or no more than 19 mW/cm² so that the system's irradiance is well within the ANSI safety guidelines for human subjects. The choice of conservative irradiance is not expected to compromise the clinical applicability of TRUE technology described herein. According to preliminary data, an irradiance of 9.5 mW/cm² on the retina is already 127 times higher than the required irradiance (75 μW/cm²) to realize TRUE focusing robustly, which is well above the perception sensitivity discussed above. Through a cataractous lens, the retinal irradiance decreases according to the level of the lens turbidity. However, a turbid cataractous lens that attenuates as much as 127 would still transmit sufficiently bright stimuli for successful use of the TRUE system.

This low intensity is more than sufficient for stimulation of the infant retina. Brown et al. (1987)[69] report that the visual acuity of human infants is maximal at luminance levels at and above 1 cd/m², which produces about 10³ photons/cone-sec. Cones have a collection area of about 1 μm², so the power needed for maximal visual acuity is 0.037 μW/cm² on the retina. This power is a tiny fraction, 0.0004% (or 4×10⁻⁶), of the safety limit of 9.5 mW/cm². Even a background that is 3 orders of magnitude brighter would only be 0.4% of the safety limit. Additionally, newborns have moderately high contrast sensitivity, so targeting a PBR of 9 (80% contrast) ensures we are well within their perceptive range.[70,71]

The safety limits for cumulative ocular exposure to light are well described as a function of radiant power, wavelength and duration.[65-68,72] Thermoacoustic damage occurs with pulses less than a nanosecond, which are not used in the TRUE technology and hence not applicable. In one example using both the maximum irradiance (9.5 mW/cm²) and the lowest contrast required for treatment (80%), and assuming that light fills up the retina (~1.8 cm²), the radiant power on the retina was computed to be 1.9×10⁻³ W. From FIG. 7, the safe exposure time is infinity. In other words, based on the ANSI standards for the chosen wavelength and the maximum irradiance proposed for the TRUE system, the safe duration of exposure is unlimited.

6. Ultrasound Sources According to One or More Embodiments

Because the eye can be vulnerable to mechanical and thermal damage from excessive ultrasonic intensity and energy, potential mechanical and thermal ultrasound effects are analyzed so can prevented if necessary by observing two indices. (1) Mechanical index (MI) is used for the determination of potential mechanical bioeffect of ultrasound. MI is defined as the ratio of the peak negative pressure of the ultrasound wave in MPa to the square root of the center frequency of the ultrasound wave MHz[74]. (2) Thermal index (TI) is used to determine the thermal bioeffect, measured by the temperature rise caused by the absorption of ultrasound by the exposed tissue. TI is defined as $TI = W_P/W_{deg}$, where is $W_P$ the relevant acoustic power at the place of interest, and $W_{deg}$ is the estimated power necessary to raise the tissue equilibrium temperature by 1° C. according to a chosen specific tissue model.[75] FDA and World Federation for Ultrasound in Medicine and Biology have imposed strict MI and TI limits for ocular application as MI<0.23 and TI<1.0.[73] In one or more examples, the limits MI<0.23 and TI<1.0 can be implemented with the TRUE system described herein using a calibrated needle hydrophone (HN-Series, Onda, Inc.) to measure the ultrasonic pressure at the ultrasonic focus, by controlling the center frequency of the ultrasound using a function generator, and using a thermocouple to monitor temperature. Moreover, the ultrasound used in the TRUE technology may operate in burst mode with a small duty cycle, which is defined as the ratio of the on time to the total time per period. With such a short heating duration, the local temperature rise at the ultrasonic focal point is negligible.

In an ideal ultrasonic focusing system with an infinite ultrasonic frequency, ultrasound focuses to a geometric point. However, the geometric point spreads to a finite size due to diffraction with a finite ultrasonic frequency. Here, a point spread function (PSF) is usually used to describe the impulse response of the focusing system, and its full width at half maximum (FWHM), $d_{TRUE}$, is used to quantify the spread.

In one or more examples, a small $d_{TRUE}$ is used to form a single line with a sharp edge. In a TRUE system, the minimum focal spot diameter is typically determined by the diffraction limit: $d_{TRUE} = 0.5\lambda_{sound}/NA_{sound}$, where $\lambda_{sound}$ is the wavelength of the ultrasound in the medium and $NA_{sound}$ is the numerical aperture (NA) of the focusing system (NA multiplied by f-number equals ½). Therefore, it is desirable to maximize the NA of the system and choose ultrasound with a sufficiently short wavelength while adequate penetration is maintained.

Figure 9:
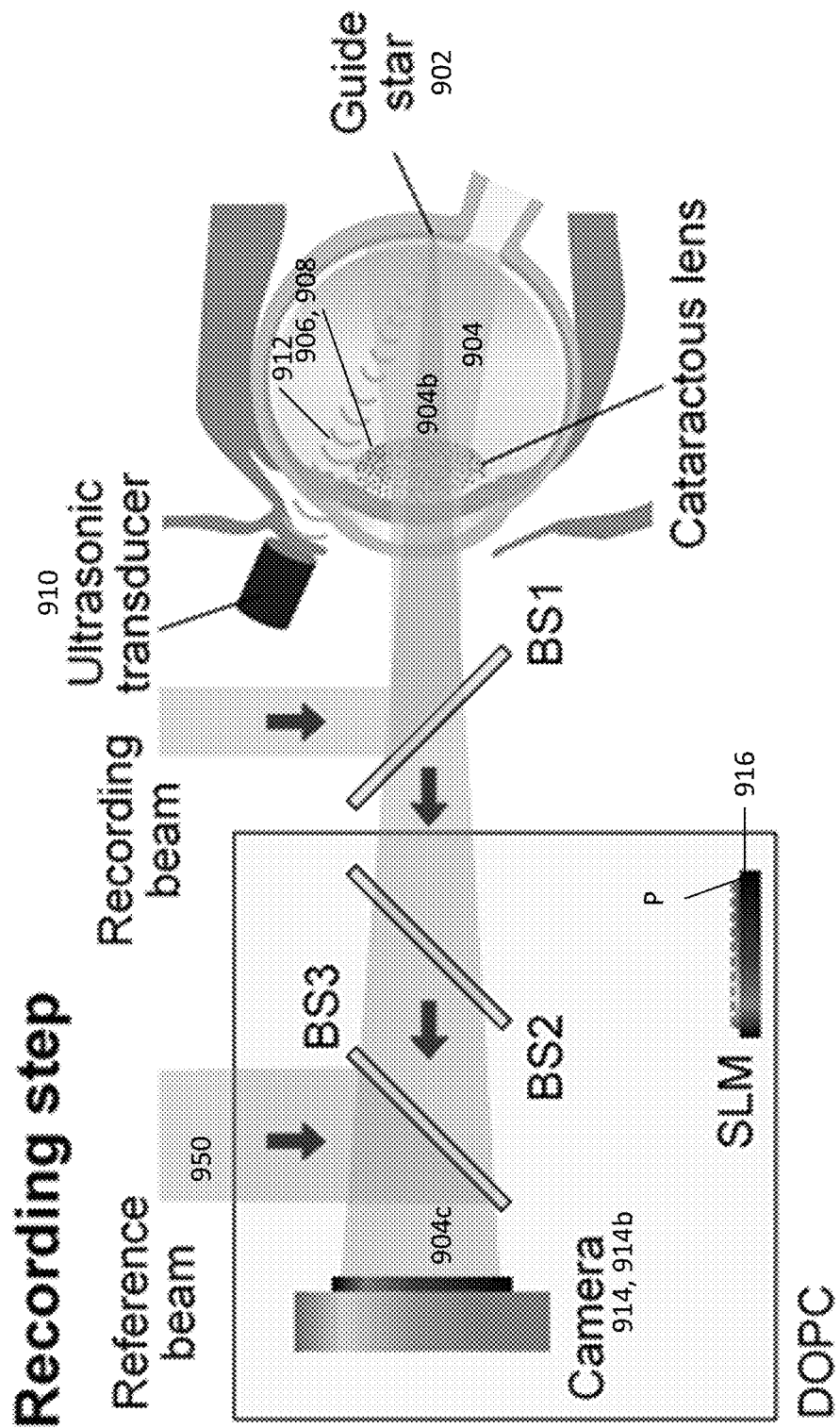
FIG. 9. Illustration of the hologram recording step for TRUE according to one or more embodiments of the present invention, where BS is a beamsplitter.

The maximum allowable NA of the ultrasonic focusing system can be determined by examining the parameters of the human eye. FIG. 9 shows the anatomy of a typical infant eye. In one or more examples, the total axial length from the anterior chamber to the retinal surface is around L=17 mm. In this example, an ultrasonic transducer is placed on the eyelid, pointing to the retina and the acoustic axis (dashed line) has a small angle of roughly 15° with respect to the centerline (dash-dotted line). Therefore, in one or more examples, the ultrasonic focal length F is chosen to be 17.6 mm, which is roughly the same as the length of the dashed line (17 mm/cos 15°), the maximum allowable radius (e.g., limited by the size of the eyelid) of the ultrasonic transducer $r_{sound}$=2.65 mm, and therefore, the maximum allowable $NA_{sound}$=sin(arctan($r_{sound}$/F))=0.149.

To use ultrasound with a short wavelength, high-frequency ultrasonic transducers can be used. In practice, due to the acoustic attenuation inside biological tissues, there exists a tradeoff between the focal spot diameter and the penetration depth. For soft tissues, the empirical rule is that the product of the penetration depth (cm) and the center frequency (MHz) of the ultrasound is about 30. Providing a penetration depth equal to F=17.6 mm, the highest center frequency of the ultrasonic transducer we can use is about 17 MHz. Fortunately, in the human eye, most of the acoustic paths are within vitreous humor. Per Amin (1989),[77] the ultrasound attenuation coefficient in vitreous humor is ~10 times less than that in soft tissues. Therefore, ultrasonic transducers with center frequencies much higher than 17 MHz can be used. In other embodiments, ultrasonic transducers with center frequencies ranging from 75 MHz to 125 MHz may be used.

Table 1 lists example focal spot diameters for the TRUE systems based on different ultrasonic transducers. Due to the oblique incidence of the ultrasound, the focal spot becomes an ellipse rather than a circle. The focal spot minor diameter along the horizontal direction (FIG. 9) remains to be $d_{TRUE}$, while the focal spot major diameter along the vertical direction (FIG. 9) is extended to $d_{TRUE}$/cos 15°. However, the differences between the minor diameter and the major diameter are always very small and in one or more examples the anisotropy can be ignored so as to use only the values of the minor diameters.

TABLE 1

List of ultrasonic wavelengths and focal spot sizes for ultrasonic transducers with different center frequencies, according to one or more examples.

|  | Center frequency (MHz) | | |
| --- | --- | --- | --- |
|  | 75 | 100 | 125 |
| Wavelength $\lambda_{sound}$ (μm) | 20 | 15 | 12 |
| Focal spot minor diameter $d_{TRUE}$ (μm) | 67.1 | 50.3 | 40.3 |
| Focal spot major diameter $d_{TRUE}$/cos15°(μm) | 69.5 | 52.1 | 41.7 |

7. Focusing Contrast of TRUE Focus According to One or More Examples

To quantify the brightness of the focus, a term called "peak-to-background ratio" (PBR) has been widely used in the literature. PBR is defined as the ratio of the peak intensity of the focus to the mean intensity of the speckles in the background. Theoretically, PBR=ηN/M, where N is the number of pixels of the SLM (also called the number of independent controllable elements) and M is the number of speckle grains within the TRUE focus. Here, η is a constant determined by the wavefront modulation scheme adopted in the system. For phase-only, binary-phase, and binary-amplitude modulations, η=π/4, 1/π, and 1/(2π), respectively.

Among physicians, "contrast number"—defined as the ratio between the difference and sum of the peak and background intensities—is commonly used. Contrast number is directly related to PBR: contrast number=(PBR−1)/(PBR+1). In one or more examples, to prevent amblyopia, a TRUE focus achieves at least a contrast number of 80%, which corresponds to a PBR of 9. To get a high contrast number or a high PBR, N can be maximized and M can be minimized.

(i) Tradeoff Between the Number of Controllable Elements (N) and the System Speed, According to One or More Examples A fast TRUE system is highly desirable in some examples in order to render images in real time and accommodate for microsaccades, respiration, and other movements. The speed of a TRUE system according to one or more embodiments is limited by the speeds of the cameras, data transfer, data processing, and SLMs. Decreasing the number of pixel counts of the electronic devices has been demonstrated as an effective way to speed up TRUE systems; however, it also degrades the focusing contrast accordingly. Therefore, there exists a tradeoff between the pixel counts of the electronic devices (both the SLMs and the cameras) and the system speed.

To accommodate most circumstances, the following example systems may be used.

(1) System 1: A first system comprising high-speed SLM (HSP1920, Medowlark, 1920×1152) integrated with a scientific complementary metal-oxide-semiconductor (sCMOS) camera (pco.edge 5.5, PCO AG). This system supports 2.21×10$^6$ independent controllable elements with a system runtime of 11.5 ms.

(2) System 2: A second system[24] which integrates a ferroelectric-based SLM (A512-P8, Medowlark, 512×512) and a scientific CMOS camera (pco.edge 5.5, PCO AG). This system supports 2.62×10$^5$ independent controllable elements with a system runtime of 7.0 ms.

Both systems uses a double-exposure binary wavefront measurement method[24] and adopts binary-phase modulation. The first system supports about 8 times more independent controllable elements but is about two times slower.

(ii) Estimation of the Number of Speckle Grains within the TRUE Focus (M), According to One or More Embodiments When light passes through highly scattered cataractous lens, scattered light forms a speckle pattern on the retina, which looks like a grainy image. The FWHM of the autocovariance function of this speckle pattern is defined as the diameter of the speckle size $d_{speckle}$, which can be physically understood as the average size of these speckle grains. Consequently, the number of speckle grains inside the TRUE focus can be estimated as M=($d_{TRUE}$/$d_{speckle}$)$^2$. Using the speckle theory,[78] $d_{speckle}$=$\lambda_{light}$L/$d_{light}$=1.35 μm, where the wavelength of light inside the eye $\lambda_{light}$=(0.532/1.34) μm=0.397 μm and the spot diameter at the posterior surface of the cataractous lens $d_{light}$=5 mm.

(iii) Estimation of the Focusing Contrast According to One or More Embodiments

Table 2 summarizes the example focusing contrast for TRUE foci obtained using different ultrasonic transducers. As seen from the table, in all situations, the PBRs are much higher than 9 and the contrast numbers are always well above 80%,

TABLE 2

Summary of the example key parameters of TRUE systems according to one or more embodiments.

|  | System 1: Slower, more SLM elements | | | System 2: Faster, fewer SLM elements | | |
|---|---|---|---|---|---|---|
| # of SLM elements: N | $2.21 \times 10^6$ (=1920 × 1152) | | | $2.62 \times 10^5$ (=512 × 512) | | |
| System runtime (ms) | 11.5 | | | 7.0 | | |
| Center frequency (MHz) | 75 | 100 | 125 | 75 | 100 | 125 |
| # of modes: M | $2.47 \times 10^3$ | $1.39 \times 10^3$ | 891 | $2.47 \times 10^3$ | $1.39 \times 10^3$ | 891 |
| PBR | 285 | 506 | 789 | 33.8 | 60.0 | 93.6 |
| Contrast number | 99.3% | 99.6% | 99.7% | 94.2% | 96.7% | 97.9% | g. Recording and Playback Steps According to One or More Embodiments

Figure 10:
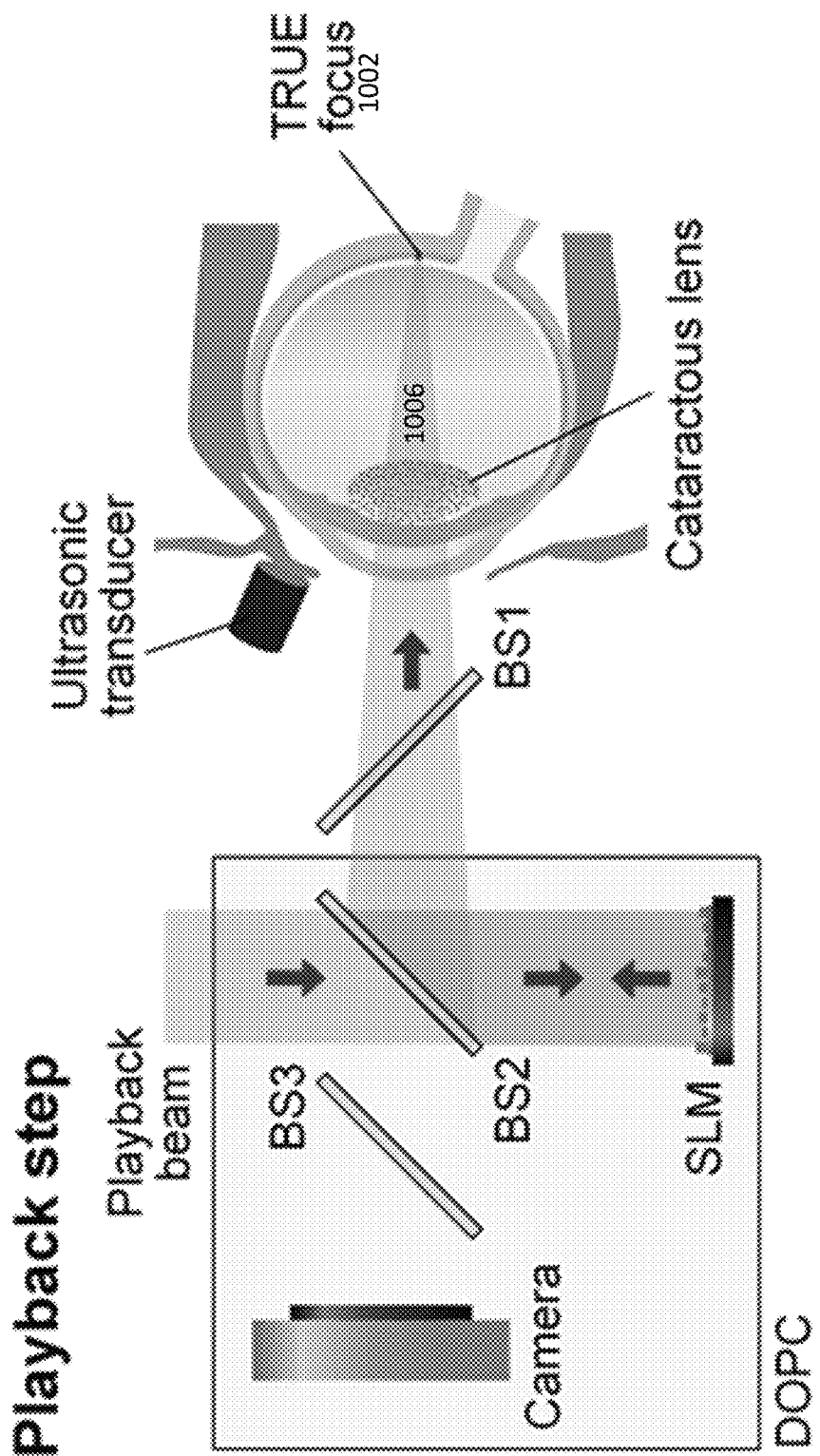
FIG. 10. Illustration of the hologram playback step for TRUE according to one or more embodiments of the present invention.

FIG. 10 illustrates the wavefront recording process of the TRUE system according to one or more embodiments. In the recording step, a recording beam (denoted in yellow) is directed to the eye, passing through the cataractous lens. Due to the highly scattering properties of the cataractous lens, light is scattered (i.e., diffused) before reaching the retina. The ultrasonic transducer forms an ultrasonic focal point anterior to the retina. Due to ultrasonic modulation, a small portion of the light that passes through the ultrasonic focus is frequency shifted (tagged, denoted in green), while the remainder of the diffused light is untagged. Both tagged and untagged light will enter the DOPC module. In general, untagged light is orders of magnitude stronger than the tagged light. In one or more examples, to isolate the useful information from the strong background, heterodyne holography is used to select the tagged light.[76] The strong heterodyne gain provided by the reference beam boosts the signal strength contributed by the tagged light, and allows the tagged light to be detected accurately by a camera. The camera-captured holographic images are then sent to the computer for processing, and the wavefront of the tagged light is computed.

Figure 11:
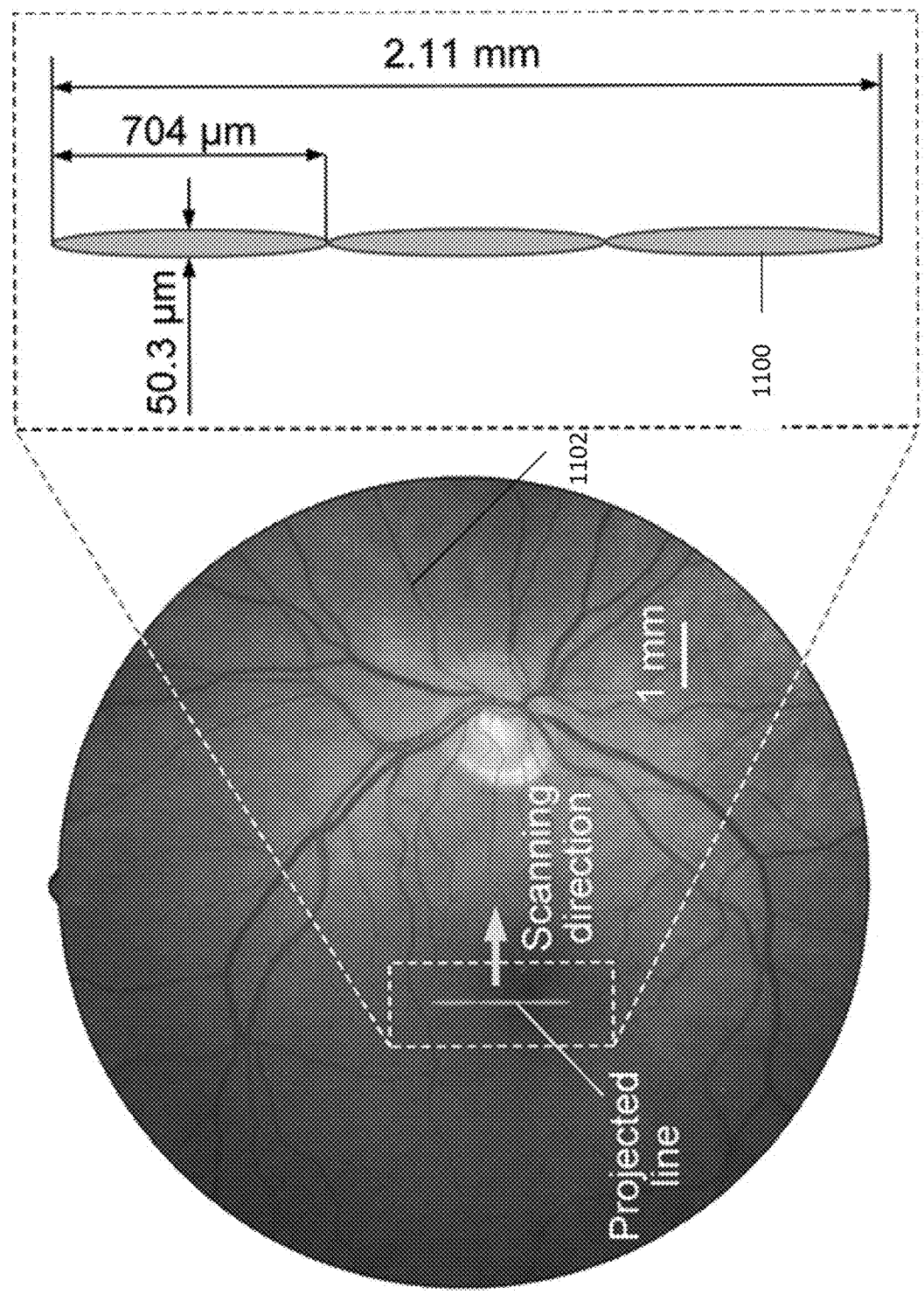
FIG. 11. Illustration of a projected bar on the human retina according to one or more embodiments of the present invention. The projected bar, i.e., a single line, is generated by using an ultrasonic transducer with a 100-MHz center frequency, as an example. Within the duration of the persistence of vision, 3 discrete TRUE foci will be successively formed; they will be perceived as a single line. The arrow indicates the scanning direction.
Figure 12:
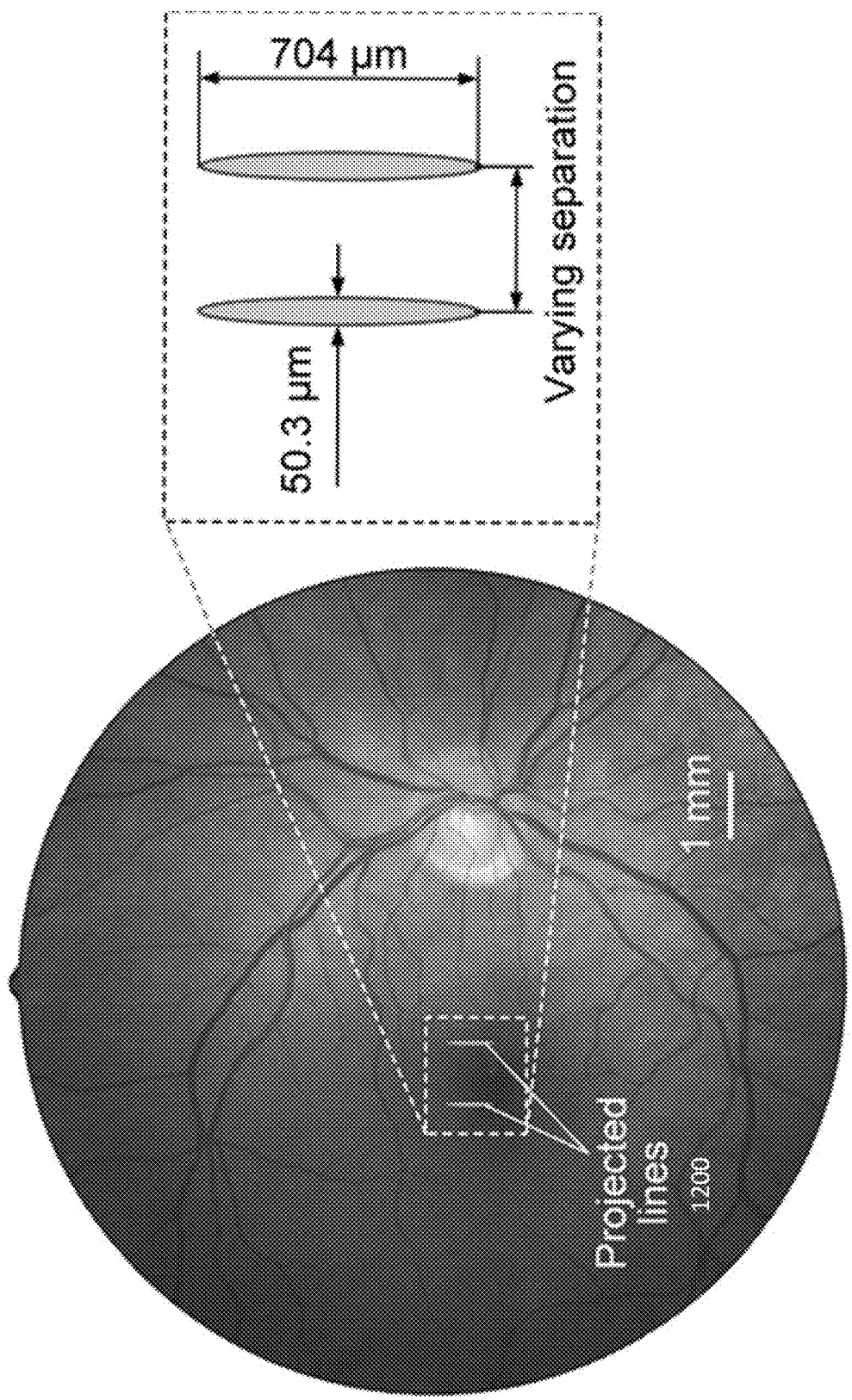
FIG. 12. Illustration of two projected bars on the human retina according to one or more embodiments of the present invention. Each projected bar is generated by using an ultrasonic transducer with a 100-MHz center frequency, as an example. Within the duration of the persistence of vision, two successively formed discrete TRUE foci will be perceived as two simultaneously projected bars. The separation can be varied and the orientation can be rotated.

FIG. 11 illustrates the wavefront playback process of the TRUE system according to one or more embodiments. In the playback step (after the recording step illustrated in FIG. 10), the playback beam with a planar wavefront is directed to the SLM, where it is modulated by the conjugated wavefront for "time reversal". Due to the time-reversal symmetry, the wavefront-shaped light converges to the ultrasonic focus after passing through the cataractous lens. As a result, an optical focus is formed despite scattering. In one embodiment forming a a line, a single TRUE focus is quickly scanned at chosen locations within the human visual processing time, although other scanning patterns can be implemented as further discussed below.

8. Stimulus Selection According to One or More Embodiments.

In the absence of appropriate stimulation during a critical period in early life, responses of neurons in the visual cortex deteriorate[21], as does vision as tested behaviorally.

Likely, moving light or dark bars are an optimal stimulus for nearly all neurons in the visual cortex when presented at the orientation appropriate for each particular neurons (although other stimuli may also be used). Stryker et al. (1978)[41] found that brief daily stimulation with bars of only one orientation (either horizontal or vertical) in otherwise visually deprived cats preserved responsiveness and selectivity in about one third of cortical neurons, with the remaining neurons becoming unresponsive or non-selective. In contrast, stimulation with bars of two different orientations (horizontal and vertical) preserved near-normal function in about two thirds of the neurons in the primary visual cortex. These defects in cortical function had corresponding behavioral consequences for vision.[80] These findings indicate that stimulation with light or dark bars is sufficient to preserve visual function for stimuli at orientations near that of the bars to which the animal was exposed. Similarly, daily exposure to only one direction of movement during early life altered the directional responses of cortical cells.[81]

Bar stimuli can be presented either as flashed or moving gratings or as single bars. Visual cortical responses, however, are selective for spatial frequency and direction of motion as well as for stimulus orientation, and no one spatial frequency will activate the majority of neurons. In human infants in particular, spatial frequency selectivity changes during early life.[70] Moving bars have the advantage that they sweep over the receptive fields and activate all neurons regardless of their selectivity for spatial frequency. In one or more examples, the stimulus selected to preserve vision comprises thin bars of light ~10 degrees (2 mm) long are swept across the central 20 degrees of the visual field at random orientations at a speed of 10 deg/sec.

In one or more examples, the TRUE system is used to present gratings, which are appropriate for eliciting pattern-visual cortical evoked potentials (pVEPs). Pattern VEPs can be elicited using two parallel bars of light, each shorter than the bar used for moving stimuli, spaced at varying distances. In one example eliciting a pattern pVEP used to interrogate central visual function, a pair of bars presented initially at 4-degree (800 μm) spacing is alternated at 4 Hz with an identical pair of bars displaced by half of the spacing. This stimulus is roughly equivalent to a contrast reversing grating at a spatial frequency of 0.25 cycles/deg and temporal frequencies between 1 Hz and 4 Hz can be used for eliciting pVEPs in human infants.[70] To measure the minimal angle of resolution using the pVEP, the spacing between the lines can be reduced until the pVEP disappears. While grating pVEPs do not correspond well to behavioral measures of optotype in amblyopic adult subjects,[82] they are a measure that is conventionally used for studies of visual development.

9. Stimulus Pattern Generation According to One or More Examples (i) Ellipsoidal Acoustic Lens According to One or More Examples In this example, a stimulus pattern comprising a sweeping single line is used to effectively stimulate the infants' retina and help them develop normal vision through opacity. An ellipsoidal acoustic lens that imposes a much less focused constraint in one direction is used to elongate the TRUE focus along one direction so as to form the TRUE focus having an ellipsoidal shape. Table 4 lists key example parameters of an example TRUE system using different ultrasonic transducers with ellipsoidal acoustic lenses. The aspect ratio of the ellipsoidal acoustic focus is 14:1. Other choices of aspect ratios can be computed similarly. In one or more examples, System 1 is used. System 1 with $2.21 \times 10^6$ independent controllable elements and 11.5 ms system runtime achieves satisfactory PBRs and a contrast number higher than 9 and 80%, respectively.

In another example, the length of the stimulus pattern is further extended through scanning. Patterns can be formed by scanning the TRUE focus within the duration of the persistence of vision. This principle is how cathode ray tube televisions generate images: for example, a single dot moving linearly within the human visual processing time, approximately 20-35 ms, is perceived as a line.[83] Because System 1 takes ~11.5 ms to form a TRUE focus, three foci can be formed within the duration of the persistence of vision. As a result, the length of the stimulus pattern, i.e., a single line, can be extended by a factor of 3, and the final dimensions of the single line are listed in the last row of Table 4.

An illustration of the single line generated by using an ultrasonic transducer with a 100-MHz center frequency is shown in FIG. 11. In one or more examples, after making this 2-mm stimulus, the line is swept perpendicularly at a speed of 2 mm/second, or 70 microns per bar presentation (at 28.5 Hz). The speed of the sweeping line can be modified. In one or more examples, the translational movement is accomplished using two motorized linear stages. In one or more examples, the single line can also be rotated over an angle range of 0-180°. This rotation procedure can be accomplished using a high-precision motorized rotational stage, for example.

TABLE 3

Example key parameters of an exampleTRUE system using different ultrasonic transducers with ellipsoidal acoustic lenses. The horizontal and vertical NAs of the ellipsoidal acoustic lenses are 0.149 and 0.0106, respectively. This system supports $2.21 \times 10^6$ (=1920 × 1152) SLM elements. Given a system runtime of 11.5 ms, a total number of 3 discrete focal points can be scanned within 35 ms.

| | System 1 with an ellipsoidal acoustic lens Center frequency (MHz) | | |
|---|---|---|---|
| | 75 | 100 | 125 |
| Horizontal diameter | 67.1 μm | 50.3 μm | 40.3 μm |
| Vertical diameter | 0.939 mm | 0.704 mm | 0.564 mm |
| # of modes: M | $3.46 \times 10^4$ | $1.94 \times 10^4$ | $1.25 \times 10^4$ |
| PBR | 20.3 | 36.3 | 56.3 |
| Contrast number | 90.6% | 94.6% | 96.5% |
| Line (width × length) | 67.1 μm × 2.82 mm | 50.3 μm × 2.11 mm | 40.3 μm × 1.69 mm |

(ii) Spherical Acoustic Lens According to One or More Examples

In another example using a spherical acoustic lens, a round TRUE focus is formed with a system runtime of 7 ms. In one or more examples, System 2 is used. Due to the higher speed of System 2, approximately 5 discrete TRUE foci can be generated during 35 ms. This system also supports $2.62 \times 10^5$ independent controllable elements. Table 5 lists the key parameters of the designed TRUE systems using different ultrasonic transducers with spherical acoustic lenses. As we can see from the table, we can still generate a single line with a length of several hundred microns while maintaining a contrast greater than 80%.

A special type of "lock-in" camera (heliCam C3, Heliotis) can measure a wavefront within 0.3 ms[84]. System 2 may be integrated with this lock-in camera to shorten the total system runtime to within 1.5 ms. Under this condition, roughly 23 TRUE foci can be formed within 35 ms, thus potentially extending the length of the single line into the millimeter region.

TABLE 5

Example key parameters of a TRUE system (7 ms) coupled with different ultrasonic transducers with spherical acoustic lenses. The NAs of these spherical acoustic lenses are 0.149. This system supports $2.62 \times 10^5$ (= 512 × 512) SLM elements. Given a system runtime of 7.0 ms, a total number of 5 discrete focal points can be scanned within 35 ms.

| | System 2 with a spherical acoustic lens Center frequency (MHz) | | |
|---|---|---|---|
| | 75 | 100 | 125 |
| Diameter | 67.1 μm | 50.3 μm | 40.3 μm |
| # of modes: M | $2.47 \times 10$ | $1.38 \times 10^3$ | 891 |
| PBR | 33.8 | 60.4 | 93.6 |
| Contrast number | 94.2% | 96.7% | 97.9% |
| Line (width × length) | 67.1 μm × 336 μm | 50.3 μm × 251 μm | 40.3 μm × 202 μm |

(iii) Further Examples: Using an Optical Scattering Map

In almost all in vivo applications, blood flow through the vessels and contraction of soft tissues are the major sources for speckle decorrelation. Since no blood vessels exist along the visual pathway and the lens is rigid, the speckle correlation can be maintained for a long period. Therefore, an "optical scattering map" of the entire lens can be generated using a pre-calibration process by focusing light at different parts of the retina and storing the corresponding phase maps. This step allows us to rapidly move the focus and project light across the retina without any additional time required for generating the guide star, measuring the hologram, transferring the data, and computing the phase map. Rather, we can rely on the predetermined scattering parameters for each area of the lens/retina axis, and only the time for the SLM to switch patterns matters. Digital micromirror device (DMD), a special type of SLM, is a viable device for this purpose. Although DMD still suffers from a relatively slow data transfer rate, it is able to switch the preloaded patterns at an extremely high rate, up to 23 kHz. In this way, we can generate 35 ms×23 kHz=805 TRUE foci within the duration of the persistence of vision. This many foci are enough to form a single line or even a more complex grating pattern on the retina. No mechanical scanning of the ultrasonic transducer is required during image projection after the pre-calibration.

10. Resolution Testing According to One or More Examples

Figure 13:
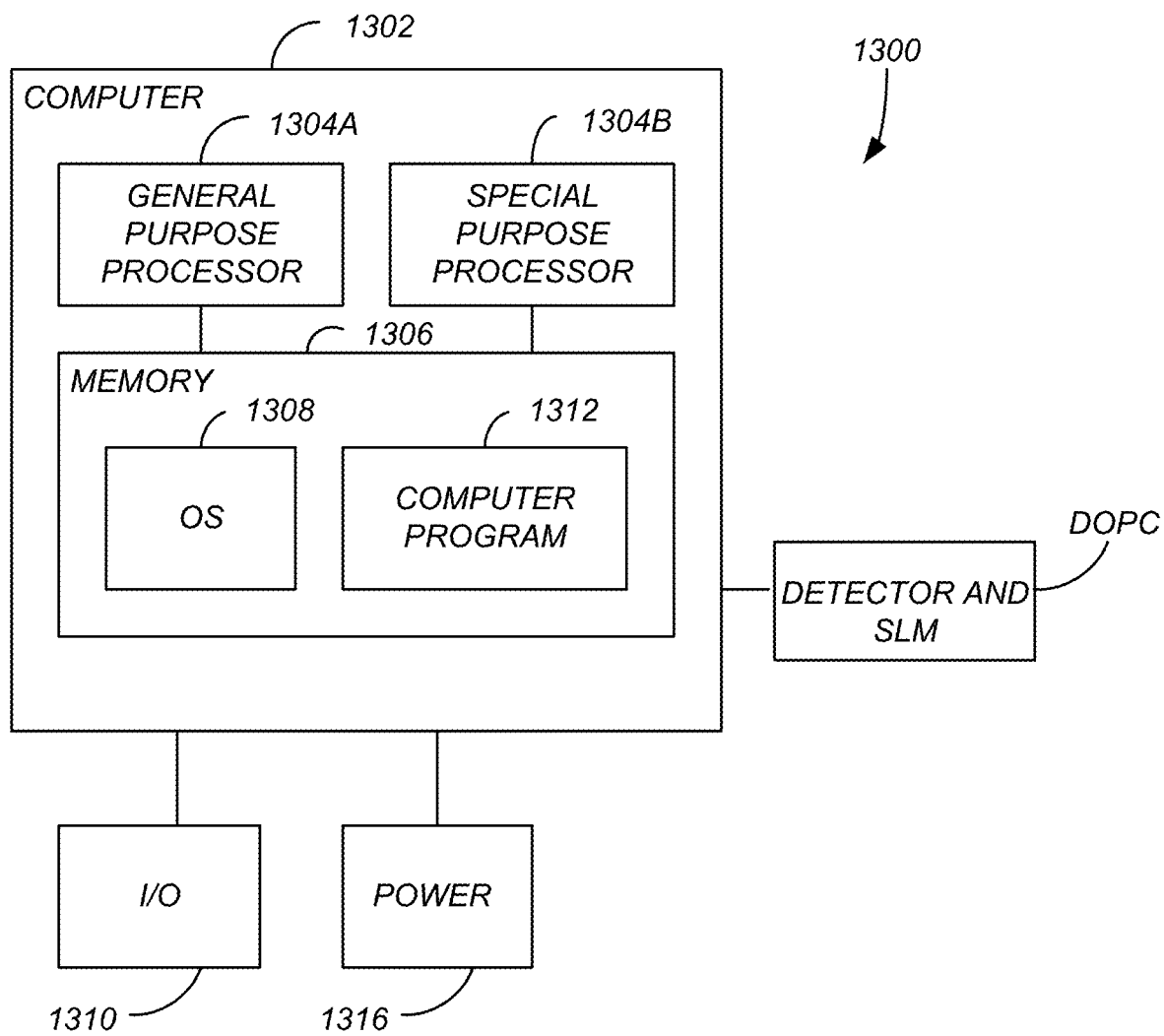
FIG. 13 illustrates a hardware environment for performing various processing methods described herein.

In one or more examples, the visual acuity of the subject is tested using two short parallel lines separated with a varying distance and projected onto the infant's retina. In one or more examples, to fulfill this requirement, the single long line generated by System 1 is separated into two short lines, as illustrated in FIG. 13. In Persistence of vision enables the generation of two parallel ellipsoidal TRUE foci sequentially within 35 ms. In one or more examples, the starting separation between the two short lines is 1 mm, corresponding to 5 deg of visual angle or a spatial frequency of 0.2 cycles/deg, where contrast sensitivity is highest at 4 postnatal weeks.[70] In one or more examples, generating the two short lines takes 11.5×2 ms=23 ms, which leaves (35−23) ms=12 ms for translating the ultrasonic transducer. Therefore, in this example, the scanning speed of the line has to be 1 mm/12 ms=83.3 mm/s, which is far less than the maximum speed of the translation stages. Table 6 lists example dimensions (width×length) of the generated testing bars. The separations between the two bars can be continuously tuned by programing the control codes for the high-performance motorized stages.

TABLE 6

Example Dimensions of the testing patterns generated using System 1 (11.5 ms system runtime) with ellipsoidal acoustic lenses. The parameters of the TRUE foci, such as the PBR and contrast number, are the same as the ones shown in Table 4.

| | System 1 with an ellipsoidal acoustic lens Center frequency (MHz) | | |
|---|---|---|---|
| | 75 | 100 | 125 |
| Line (width × length) | 67.1 μm × 0.939 mm | 50.3 μm × 0.704 mm | 40.3 μm × 0.564 mm |

11. Process Steps a. Processing Environment

FIG. 13 illustrates an exemplary system 1300 used to implement processing elements described herein including, but not limited to, processing elements needed to measure the scattered field, determine the output field, and/or control the modulator (e.g., SLM) so as to modulate the output electromagnetic radiation with the output field.

The computer 1302 comprises a processor 1304 (general purpose processor 1304A and special purpose processor 1304B) and a memory, such as random access memory (RAM) 1306. Generally, the computer 1302 operates under control of an operating system 1308 stored in the memory 1306, and interfaces with the user/other computers to accept inputs and commands (e.g., analog or digital signals from the crew or automatic ice detector) and to present results through an input/output (I/O) module 1310. The computer program application 1312 accesses and manipulates data stored in the memory 1306 of the computer 1302. The operating system 1308 and the computer program 1312 are comprised of instructions which, when read and executed by the computer 1302, cause the computer 1302 to perform the operations and/or methods herein described. In one embodiment, instructions implementing the operating system 1308 and the computer program 1312 are tangibly embodied in the memory 1306, thereby making one or more computer program products or articles of manufacture capable of determining a phase and/or amplitude of the output electromagnetic radiation from the recording; determining the output field of the output electromagnetic radiation comprising a phase conjugate of the scattered field of the scattered electromagnetic radiation; determining a phase and/or amplitude of the scattered field of the scattered electromagnetic radiation; and/or modulating the pixels on the modulator (SLM) so as to form the output electromagnetic radiation comprising the output (e.g., electric) field. As such, the terms "article of manufacture," "program storage device" and "computer program product" as used herein are intended to encompass a computer program accessible from any computer readable device or media. In one embodiment, the special purpose processor 1304B is an application specific integrated circuit (ASIC). In one or more embodiments, computer 1302 may be coupled to, or may comprise, a personal computer (e.g., desktop computer (e.g., HP Compaq™), portable or media viewing/listening device (e.g., cellular/mobile device/phone, laptop, tablet, personal digital assistant, etc.) or integrated circuit, chip, or field prorgammable gate array (FPGA). In yet another embodiment, the computer 1302 may comprise a multi-touch device, gaming system, or other internet enabled device executing on various platforms and operating systems.

Those skilled in the art will recognize many modifications may be made to this configuration without departing from the scope of the present disclosure. For example, those skilled in the art will recognize that any combination of the above components, or any number of different components, peripherals, and other devices, may be used.

b. Method of Fabrication

Figure 14:
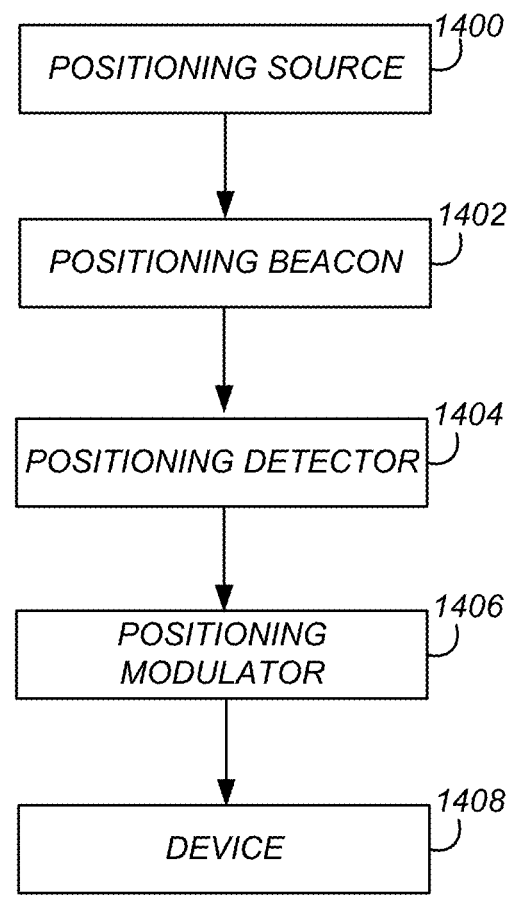
FIG. 14 is a flowchart illustrating a method of making a device according to one or more embodiments of the present invention.

FIG. 14 is a flowchart illustrating a method of making a device 900 for irradiating ocular tissue (referring also to FIG. 2, FIGS. 4-6 and FIGS. 9-12.

Block 1400 represents positioning a source 601 of electromagnetic radiation 602 (e.g., a laser). Examples of electromagnetic radiation 602 include light having a wavelength in the visible or infrared wavelength spectrum (e.g., green light).

Block 1402 represents positioning a beacon 902 scattering the portion 904 of electromagnetic radiation 602 transmitted through an opacity 906 in ocular tissue 908 so as to form scattered electromagnetic radiation 904b. In one or more examples, the step comprises positioning a transmitter 910 of ultrasound (e.g., ultrasonic transducer) positioned so as to transmit ultrasound 912 forming the beacon 902 including a focus 1002 of the ultrasound 912, wherein the ultrasound's 912 frequency shifts the electromagnetic radiation 904 transmitted through the opacity 906 so as to form the scattered electromagnetic radiation 904b comprising frequency shifted electromagnetic radiation.

Block 1404 represents positioning a detector 914 (e.g., wavefront sensor or camera). The detector 914 outputs a signal comprising the recording in response to the scattered electromagnetic radiation 904c received on the detector 914. In one or more examples, the signal comprises an interference pattern recording interference between the scattered field of the scattered electromagnetic radiation 804c and a reference beam 950 incident on the detector 914. In one or more examples, the detector comprises a detection system measuring a phase and/or amplitude of the scattered field of the scattered electromagnetic radiation 904c using phase shifting holography, and the computer 1300 determines the output field from the phase and/or amplitude of the scattered field.

Block 1406 represents optionally positioning and configuring a modulator 916 capable of transmitting output electromagnetic radiation having a field determined from a recording of the scattered electromagnetic radiation 904b (or portion 1006 of the scattered electromagnetic radiation 904b) transmitted through the opacity 906, so that the output electromagnetic radiation 1006 is transmitted through the opacity 906 to the beacon 902.

Block 1408 represents the end result, a device 900 for irradiating ocular tissue 908.

The device can be embodied in many ways including, but not limited to, the following.

1. A device 200 for irradiating ocular tissue, comprising a source 601, 202 of electromagnetic radiation 602,204; a beacon 902, 206 scattering or tagging the electromagnetic radiation 904, 208 transmitted through an opacity 906, 210 in ocular tissue 908, 212 so as to form scattered electromagnetic radiation 904b, 214; and a modulator 916, 216 transmitting output electromagnetic radiation 1006, 218 having a field and/or wavefront 220 determined from a recording of the scattered electromagnetic radiation 222 transmitted through the opacity 906, so that the output electromagnetic radiation 1006, 218 is transmitted through the opacity 906, 210 to the beacon 902, 206.

2. The device of embodiment 1, wherein the ocular tissue 908 comprises lens tissue comprising cataractous tissue 502, 228 or other light scattering media 804 in/intersecting with the optical axis 810 of an eye 504. In one or more examples, cataractous tissue or cataractous lens is a lens or tissue comprising a cataract.

3. The device of one or any combination of embodiments 1-2, wherein the beacon 902 is positioned on retinal tissue 802, 230.

4. The device of one or any combination of the previous embodiments 1-3 further comprising a transmitter 910 of ultrasound 912 positioned so as to transmit ultrasound forming the beacon 902 including a focus 1002 of the ultrasound 902, wherein the ultrasound 912 frequency shifts the electromagnetic radiation 904 transmitted through the opacity 906 so as to form the scattered electromagnetic radiation 904b comprising frequency shifted electromagnetic radiation.

5. The device of one or any combination of the previous embodiments 1-4, wherein the output electromagnetic radiation 1006 comprises a phase conjugate of the scattered electromagnetic radiation 904c transmitted through the opacity 906.

6. The device of one or any combination of the previous embodiments 1-5, further comprising a detector 914 outputting a signal comprising the recording in response to the scattered electromagnetic radiation 904c received on the detector 914; and a computer 1302 connected to the detector 914 and the modulator 916. The computer 1302 determines a phase, an amplitude, or an amplitude and a phase of the output electromagnetic radiation 1006 from the recording; and the modulator 916 modulates the output electromagnetic radiation 1006 so that the output electromagnetic radiation has the phase, the amplitude, or the amplitude and the phase.

7. The device of embodiment 6, wherein the detector 914 comprises a wavefront sensor 914b measuring a wavefront for each spatial location in the scattered electromagnetic radiation 1006 associated with a stimulation pattern 1100; the computer 1302 synthesizes an output wavefront of the output electromagnetic radiation 1006 using the wavefront; and the modulator 916 modulates the output electromagnetic radiation 1006 so as to transmit the stimulation pattern 1100 to the beacon 902.

8. The device of one or any combination of the previous embodiments 6-7, wherein the modulator 916 comprises pixels P that are sequentially modulated so as to scan the output electromagnetic radiation 1006 representing different points in the stimulation pattern 1100 across retinal tissue 802 within a duration of persistence of vision so that a human or animal subject perceives the stimulation pattern 1100, wherein the beacon 902 is on the retinal tissue 802, and/or the computer 1302 uses an optical memory effect to determine the output wavefronts for neighboring points in the stimulation pattern 1100 by adding different phase gradients so as to reduce a number of the wavefronts measured by the wavefront sensor.

9. The device of one or any combination of the previous embodiments 6-8, wherein the modulator 916 comprises pixels P, wherein the pixels P have variable transmissivity, reflectivity, or emission so as to modulate an intensity of the output electromagnetic radiation 1006 transmitted from the pixels P, the computer 1302 controls the transmissivity, reflectivity, or emission of each of the pixels P so as to form a varying intensity comprising a stimulating pattern 1100 capable of stimulating nerves 1102 on retinal tissue 802, and the beacon 902 is on the retinal tissue 802.

10. The device of one or any combination of the previous embodiments 6-9, wherein the computer 1302 determines, from the signal, values representing a phase, an amplitude, or a phase and an amplitude of the scattered electromagnetic radiation 904c at spatial locations associated with the stimulating pattern 1100; and the computer 1302 determines the phase, an amplitude, or the amplitude and the phase of the output electromagnetic radiation 1006 from the values.

11. The device of one or any combination of the previous embodiments 7-10, wherein the stimulating pattern 1100 comprises a line.

12. The device of embodiment 11, wherein the stimulating pattern comprises a pair of lines 1200 moving closer together so as to measure visual acuity.

13. The device of one or any combination of embodiments 7-12, wherein the computer 1302 temporally controls the transmissivity, reflectivity, or emission of each of the pixels P so that all points or regions of the stimulating pattern 1100 are transmitted from the modulator sequentially in time, e.g., within a duration of 50 milliseconds or within a duration of a persistence of vision of an infant.

14. The device of one or any combination of embodiments 7-13, wherein the computer 1302 determines, from the signal, values representing a phase, an amplitude, or a phase and an amplitude of the scattered electromagnetic radiation 904c for a subset of spatial locations associated with the stimulating pattern 1100; and the computer 1302 uses an optical memory effect to calculate the phase and/or amplitude for neighboring points in the stimulating pattern 1100 by adding different phase gradients.

15. A device 900 for irradiating ocular tissue, comprising a source of electromagnetic radiation 602; a beacon 902 scattering the electromagnetic radiation 904 transmitted through ocular tissue so as to form scattered electromagnetic radiation 904b; a wavefront sensor 914b measuring a phase and/or amplitude of the scattered electromagnetic radiation 904c transmitted through the opacity; and a computer 1302 mapping optical properties at different spatial locations across the ocular tissue 908 using the phase and/or amplitude.

16. The device of embodiment 15, wherein the ocular tissue comprises lens tissue comprising cataractous tissue 502 or other light scattering media in the optical axis 510, 810 of an eye 504.

17. The device of one or any combination of embodiments 15-16, wherein the beacon 902 is positioned on retinal tissue 802, corneal tissue 804, lens tissue 806, or other light scattering media in/intersecting with the optical axis 510, 810 of the eye 504.

18. The device of one or any combination of embodiments 15-17, wherein the electromagnetic radiation 602 has a phase and amplitude selected to optically determine the optical properties comprising optical scattering of corneal or lens tissue.

19. The device of embodiment 18, wherein the optical properties are used to inform a machine (e.g., including a laser) on how to ablate the cornea to correct for optical aberrations caused by the corneal or lens tissue (e.g., on how to ablate the cornea for optical clarity).

20. The device of any one of the previous embodiments, wherein the modulator is a spatial light modulator, a digital micromirror device, or a ferroelectric modulation layer, or a ferroelectric liquid crystal based SLM.

c. Method of Operation

Figure 15:
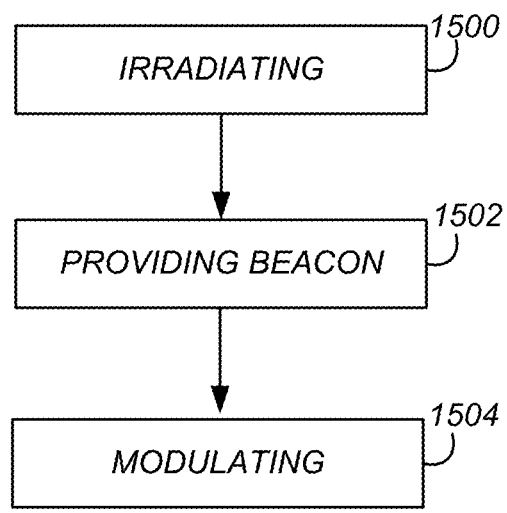
FIG. 15 is a flowchart illustrating a method of operating a device according to one or more embodiments of the present invention.

FIG. 15 is a flowchart illustrating a method of irradiating ocular tissue.

Block 1500 represents irradiating ocular tissue with electromagnetic radiation.

Block 1502 represents providing a beacon behind an opacity in ocular tissue so as to scatter the electromagnetic radiation transmitted through the opacity and form scattered electromagnetic radiation. In one or more examples, the step comprises transmitting ultrasound so as to form the beacon comprising a focus of the ultrasound, wherein the ultrasound frequency shifts the electromagnetic radiation transmitted through the opacity so as to form the scattered electromagnetic radiation comprising frequency shifted electromagnetic radiation.

Block 1504 represents modulating output electromagnetic radiation so as to form the output electromagnetic radiation having a field determined from a recording of the scattered electromagnetic radiation transmitted through the opacity, wherein the output electromagnetic radiation is transmitted through the opacity to the beacon.

In one or more examples, the output electromagnetic radiation comprises a phase conjugate of the scattered electromagnetic radiation transmitted through the opacity.

In one or more examples the modulating forms the output electromagnetic radiation comprising a stimulating pattern useful for stimulating nerves in retinal tissue, and the beacon is on the retinal tissue. In one or more embodiments, the stimulating pattern is used to treat amblyopia.

In one or more embodiments, brain waves are monitored as the stimulating pattern is applied.

In one or more embodiments electroretinogram readings are taken as the stimulating pattern is applied.

The method of irradiating may use the device of one or more embodiments described in FIG. 13.

Advantages and Improvements

As illustrated herein, TRUE focusing technology can be used to compensate for scattering using time reversal symmetry and can, in some examples, form an optical focus inside scattering media with a high resolution down to the tens of microns. This capability to tackle highly scattering media is made possible in one or more embodiments by a reliable guide star and a DOPC system that overcomes high turbidity.

Example apparatuses and methods described herein can be used to prevent the formation of amblyopia from congenital cataracts, in one or more embodiments, by projecting sharp images on the retina through the cataract using this TRUE optical focusing technology. In one or more examples, TRUE overcomes the cataract-induced scattering effect and computes the (e.g., optimum) wavefront that can achieve optical focusing at any targeted location on the retina. Then, by repeating TRUE experiments while fast scanning the ultrasonic transducer along a certain direction, a sequence of discrete TRUE foci can be formed. In one or more examples, the foci are formed within the duration of the persistence of vision (i.e., within the time in which two sequentially projected images appear as a single image, e.g., typically 20-35 ms), so as to blend in the infant's vision as a single line. In one or more further examples, line patterns with various orientations can effectively stimulate the infant's retina and help them develop normal vision. Therefore, in one or more examples, TRUE technology can be the most suitable non-invasive and robust method that is capable of projecting sharp images onto the retina through a cataract.

REFERENCES

The following references are incorporated by reference herein.

References for the First Example

The following references are incorporated by reference herein.

1. R. D. Harley, L. B. Nelson and S. E. Olitsky, *Harley's Pediatric ophthalmology*, Lippincott Williams & Wilkins (2005).

2. N. W. Daw, "Critical periods and amblyopia," *Arch. Ophthalmol.* 116(4), 502-505 (1998).

3. T. L. Lewis and D. Maurer, "Multiple sensitive periods in human visual development: Evidence from visually deprived children," *Dev. Psychobiol.* 46(3), 163-183 (2005).

4. J. M. Holmes, D. A. Leske, J. P. Burke and D. O. Hodge, "Birth prevalence of visually significant infantile cataract in a defined US population," *Ophthalmic Epidemiol.* 10(2), 67-74 (2003).

5. S. S. Gelbart, C. S. Hoyt, G. Jastrebski and E. Marg, "Long-term visual results in bilateral congenital cataracts," *Am. J. Ophthalmol.* 93(5), 615-621 (1982).

6. R. Beller, C. S. Hoyt, E. Marg and J. V. Odom, "Good visual function after neonatal surgery for congenital monocular cataracts," *Am. J. Ophthalmol.* 91(5), 559-565 (1981).

7. A. O. Khan and S. Al-Dahmesh, "Age at the time of cataract surgery and relative risk for aphakic glaucoma in nontraumatic infantile cataract," *Journal of American Association for Pediatric Ophthalmology and Strabismus {JAA-POS}* 13(2), 166-169 (2009).

8. M. Chak and J. S. Rahi, "Incidence of and Factors Associated with Glaucoma after Surgery for Congenital Cataract: Findings from the British Congenital Cataract Study," *Ophthalmology* 115(6), 1013-1018.e1012 (2008).

9. M. Vishwanath, R. Cheong-Leen, D. Taylor, I. Russell-Eggitt and J. Rahi, "Is early surgery for congenital cataract a risk factor for glaucoma?," *Br. J. Ophthalmol.* 88(7), 905 (2004).

10. A. P. Mosk, A. Lagendijk, G. Lerosey and M. Fink, "Controlling waves in space and time for imaging and focusing in complex media," *Nat. Photon.* 6(5), 283-292 (2012).

11. R. Horstmeyer, H. Ruan and C. Yang, "Guidestar-assisted wavefront-shaping methods for focusing light into biological tissue," *Nat. Photon.* 9(9), 563-571 (2015).

12. H. Yu, J. Park, K. Lee, J. Yoon, K. Kim, S. Lee and Y. Park, "Recent advances in wavefront shaping techniques for biomedical applications," *Curr. Appl. Phys.* 15(5), 632-641 (2015).

13. S. Rotter and S. Gigan, "Light fields in complex media: Mesoscopic scattering meets wave control," *Rev. Mod. Phys.* 89(1), 015005 (2017).

14. I. M. Vellekoop and A. P. Mosk, "Focusing coherent light through opaque strongly scattering media," *Opt. Lett.* 32(16), 2309-2311 (2007).

15. I. M. Vellekoop, "Feedback-based wavefront shaping," *Opt. Express* 23(9), 12189-12206 (2015).

16. S. Popoff, G. Lerosey, R. Carminati, M. Fink, A. Boccara and S. Gigan, "Measuring the transmission matrix in optics: an approach to the study and control of light propagation in disordered media," *Phys. Rev. Lett.* 104(10), 100601 (2010).

17. Y. Choi, T. D. Yang, C. Fang-Yen, P. Kang, K. J. Lee, R. R. Dasari, M. S. Feld and W. Choi, "Overcoming the Diffraction Limit Using Multiple Light Scattering in a Highly Disordered Medium," *Phys. Rev. Lett.* 107(2), 023902 (2011).

18. Z. Yaqoob, D. Psaltis, M. S. Feld and C. Yang, "Optical phase conjugation for turbidity suppression in biological samples," *Nat. Photon.* 2(2), 110-115 (2008).

19. M. Cui and C. Yang, "Implementation of a digital optical phase conjugation system and its application to study the robustness of turbidity suppression by phase conjugation," *Opt. Express* 18(4), 3444-3455 (2010).

20. C.-L. Hsieh, Y. Pu, R. Grange and D. Psaltis, "Digital phase conjugation of second harmonic radiation emitted by nanoparticles in turbid media," *Opt. Express* 18(12), 12283-12290 (2010).

21. Y. Shen, Y. Liu, C. Ma and L. V. Wang, "Focusing light through biological tissue and tissue-mimicking phantoms up to 9.6 cm in thickness with digital optical phase conjugation," *J. Biomed. Opt.* 21(8), 085001 (2016).

22. Y. Liu, P. Lai, C. Ma, X. Xu, A. A. Grabar and L. V. Wang, "Optical focusing deep inside dynamic scattering media with near-infrared time-reversed ultrasonically encoded (TRUE) light," *Nat. Commun.* 6(5904 (2015).

23. D. Wang, E. H. Zhou, J. Brake, H. Ruan, M. Jang and C. Yang, "Focusing through dynamic tissue with millisecond digital optical phase conjugation," *Optica* 2(8), 728-735 (2015).

24. Y. Liu, C. Ma, Y. Shen, J. Shi and L. V. Wang, "Focusing light inside dynamic scattering media with millisecond digital optical phase conjugation," *Optica* 4(2), 280-288 (2017).

25. C. Ma, F. Zhou, Y. Liu and L. V. Wang, "Single-exposure optical focusing inside scattering media using binarized time-reversed adapted perturbation," *Optica* 2(10), 869-876 (2015).

26. M. M. Qureshi, J. Brake, H.-J. Jeon, H. Ruan, Y. Liu, A. M. Safi, T. J. Eom, C. Yang and E. Chung, "In vivo study of optical speckle decorrelation time across depths in the mouse brain," *Biomed. Opt. Express* 8(11), 4855-4864 (2017).

27. X. Xu, H. Liu and L. V. Wang, "Time-reversed ultrasonically encoded optical focusing into scattering media," *Nat. Photon.* 5(3), 154-157 (2011).

28. Y. M. Wang, B. Judkewitz, C. A. DiMarzio and C. Yang, "Deep-tissue focal fluorescence imaging with digitally time-reversed ultrasound-encoded light," *Nat. Commun.* 3(928 (2012).

29. K. Si, R. Fiolka and M. Cui, "Fluorescence imaging beyond the ballistic regime by ultrasound-pulse-guided digital phase conjugation," *Nat. Photon.* 6(10), 657-661 (2012).

30. L. V. Wang and H. Wu, *Biomedical optics: principles and imaging*, Wiley-Interscience, Hoboken, N.J. (2007).

31. H. Ruan, M. Jang, B. Judkewitz and C. Yang, "Iterative Time-Reversed Ultrasonically Encoded Light Focusing in Backscattering Mode," *Sci. Rep.* 4(7156 (2014).

32. Y. Shen, Y. Liu, C. Ma and L. V. Wang, "Focusing light through scattering media by full-polarization digital optical phase conjugation," *Opt. Lett.* 41(6), 1130-1133 (2016).

33. Y. Liu, C. Ma, Y. Shen and L. V. Wang, "Bit-efficient, sub-millisecond wavefront measurement using a lock-in camera for time-reversal based optical focusing inside scattering media," *Opt. Lett.* 41(7), 1321-1324 (2016).

34. F. Le Clerc, L. Collot and M. Gross, "Numerical heterodyne holography with two-dimensional photodetector arrays," *Opt. Lett.* 25(10), 716-718 (2000).

35. K. Si, R. Fiolka and M. Cui, "Breaking the spatial resolution barrier via iterative sound-light interaction in deep tissue microscopy," *Sci. Rep.* 2(748 (2012).

36. Y. Suzuki, J. W. Tay, Q. Yang and L. V. Wang, "Continuous scanning of a time-reversed ultrasonically encoded optical focus by reflection-mode digital phase conjugation," *Opt. Lett.* 39(12), 3441-3444 (2014).

37. L. V. Wang and S. Hu, "Photoacoustic Tomography: In Vivo Imaging from Organelles to Organs," *Science* 335 (6075), 1458-1462 (2012).

38. Y. Liu, C. Zhang and L. V. Wang, "Effects of light scattering on optical-resolution photoacoustic microscopy," *J. Biomed. Opt.* 17(12), 126014 (2012).

39. J. Brake, M. Jang and C. Yang, "Analyzing the relationship between decorrelation time and tissue thickness in acute rat brain slices using multispeckle diffusing wave spectroscopy," *J. Opt. Soc. Am. A* 33(2), 270-275 (2016).

40. A. S. Hemphill, J. W. Tay and L. V. Wang, "Hybridized wavefront shaping for high-speed, high-efficiency focusing through dynamic diffusive media," *J. Biomed. Opt.* 21(12), 121502 (2016).

41. A. M. Caravaca-Aguirre, E. Niv, D. B. Conkey and R. Piestun, "Real-time resilient focusing through a bending multimode fiber," *Opt. Express* 21(10), 12881-12887 (2013).

References for Second Example

1. Holmes J M, Leske D A, Burke J P, Hodge D O. Birth prevalence of visually significant infantile cataract in a defined U.S. population. Ophthalmic Epidemiol. 2003 April; 10(2):67-74. PMID: 12660855

2. Foster A, Gilbert C, Rahi J. Epidemiology of cataract in childhood: a global perspective. J Cataract Refract Surg. 1997; 23:601-604.

3. Gilbert C, Foster A. Childhood blindness in the context of VISION 2020—the right to sight. Bull World Health Organ. 2001; 79(3):227-232. PMCID: PMC2566382

4. Foundation L. Amblyopia: Challenges and opportunities [Internet]. The Lasker Foundation. [cited 2018 Feb. 3]. Available from: http://www.laskerfoundation.org/new-noteworthy/articles/amblyopia-challenges/

5. Birch E E, Cheng C, Stager D R, Weakley D R, Stager D R. The Critical Period for Surgical Treatment of Dense Congenital Bilateral Cataracts. J Aapos. 2009 February; 13(1):67-71. PMCID: PMC3310432

6. Hartmann E E, Lynn M J, Lambert S R. Baseline Characteristics of the Infant Aphakia Treatment Study Population: Predicting Recognition Acuity at 4.5 Years of Age. Invest Ophthalmol Vis Sci. 2015 Jan. 1; 56(1):388-395.

7. Congenital cataract: a concise guide to diagnosis and management. New York, N.Y.: Springer Berlin Heidelberg; 2016.

8. Gelbart S S, Hoyt C S, Jastrebski G, Marg E. Long-Term Visual Results in Bilateral Congenital Cataracts. Am J Ophthalmol. 1982 May 1; 93(5):615-621.

9. Beller R, Hoyt C S, Marg E, Odom J V. Good visual function after neonatal surgery for congenital monocular cataracts. Am J Ophthalmol. 1981 May; 91(5):559-565. PMID: 7234936

10. Khan A O, Al-Dahmesh S. Age at the time of cataract surgery and relative risk for aphakic glaucoma in nontraumatic infantile cataract. J Am Assoc Pediatr Ophthalmol Strabismus. 2009 Apr. 1; 13(2):166-169.

11. Chak M, Rahi J S, British Congenital Cataract Interest Group. Incidence of and factors associated with glaucoma after surgery for congenital cataract: findings from the British Congenital Cataract Study. Ophthalmology. 2008 June; 115(6):1013-1018.e2. PMID: 18164065

12. Vishwanath M, Cheong-Leen R, Taylor D, Russell-Eggitt I, Rahi J. Is early surgery for congenital cataract a risk factor for glaucoma? Br J Ophthalmol. 2004 Jul. 1; 88(7): 905-910. PMID: 15205235

13. Chen T C, Chen P P, Francis B A, Junk A K, Smith S D, Singh K, Lin S C. Pediatric Glaucoma Surgery. Ophthalmology. 2014 November; 121(11):2107-2115.

14. Lambert S R. The timing of surgery for congenital cataracts: Minimizing the risk of glaucoma following cataract surgery while optimizing the visual outcome. J AAPOS Off Publ Am Assoc Pediatr Ophthalmol Strabismus. 2016 June; 20(3):191-192. PMCID: PMC5018898

15. Kalatsky V A, Stryker M P. New Paradigm for Optical Imaging: Temporally Encoded Maps of Intrinsic Signal. Neuron. 2003 May 22; 38(4):529-545.

16. Kaneko M, Stryker M P. Sensory experience during locomotion promotes recovery of function in adult visual cortex. eLife [Internet]. 2014 [cited 2018 Jan. 12]; 3. Available from: https://www-ncbi-nlm-nih-gov.ucsf.idm.oclc.org/pmc/articles/PMC4070284/PMID: 24970838

17. Mui A M, Yang V, Aung M H, Fu J, Adekunle A N, Prall B C, Sidhu C S, Park H na, Boatright J H, Iuvone P M, Pardue M T. Daily visual stimulation in the critical period enhances multiple aspects of vision through BDNF-mediated pathways in the mouse retina. PLoS ONE [Internet]. 2018 [cited 2018 Feb. 25]; 13(2). Available from: https://www-ncbi-nlm-nih-gov.ucsf.idm.oclc.org/pmc/articles/PMC5800661/PMID: 29408880

18. Zhang B, Tao X, Wensveen J M, Harwerth R S, Smith E L, Chino Y M. Effects of Brief Daily Periods of Unrestricted Vision during Early Monocular Form Deprivation on Development of Visual Area 2. Investig Opthalmology Vis Sci. 2011 Sep. 13; 52(10):7222.

19. Wensveen J M, Harwerth R S, Hung L-F, Ramamirtham R, Kee C, Smith E L. Brief daily periods of unrestricted vision can prevent form-deprivation amblyopia. Invest Ophthalmol Vis Sci. 2006 June; 47(6):2468-2477. PMCID: PMC1783686

20. Espinosa J S, Stryker M P. Development and Plasticity of the Primary Visual Cortex. Neuron. 2012 Jul. 26; 75(2): 230-249. PMCID: PMC3612584

21. Crair M C, Gillespie D C, Stryker M P. The Role of Visual Experience in the Development of Columns in Cat Visual Cortex. Science. 1998 Jan. 23; 279(5350):566-570. PMCID: PMC2453000

22. Liu Y, Shen Y, Ruan H, Brodie F L, Wong T T W, Yang C, Wang L V. Time-reversed ultrasonically encoded optical focusing through highly scattering <italic>ex vivo</italic> human cataractous lenses. J Biomed Opt. 2018 January; 23(1):010501.

23. Xu X, Liu H, Wang L V. Time-reversed ultrasonically encoded optical focusing into scattering media. Nat Photonics. 2011 March; 5(3):154. PMCID: PMC3083021

24. Liu Y, Ma C, Shen Y, Shi J, Wang L V. Focusing light inside dynamic scattering media with millisecond digital optical phase conjugation. Optica. 2017 Feb. 20; 4(2):280-288.

25. Harley R D, Nelson L B, Olitsky S E. Harley's Pediatric Ophthalmology. Lippincott Williams & Wilkins; 2005.

26. Daw N W. Critical Periods and Amblyopia. Arch Ophthalmol. 1998 Apr. 1; 116(4):502-505.

27. Awaya S, Sugawara M, Miyake S. Observations in patients with occlusion amblyopia: results of treatment. Trans Ophthalmol Soc U K. 1979; 99(3):447-454. PMID: 298830

28. Lambert S R, Lynn M, Drews-Botsch C, DuBois L, Plager D A, Medow N B, Wilson M E, Buckley E G. Optotype acuity and re-operation rate after unilateral cataract surgery during the first 6 months of life with or without IOL implantation. Br J Ophthalmol. 2004 Nov. 1; 88(11): 1387-1390. PMID: 15489478

29. Freedman S F, Lynn M J, Beck A D, Bothun E D, Orge F H, Lambert S R. Glaucoma-Related Adverse Events in the First 5 Years After Unilateral Cataract Removal in the Infant Aphakia Treatment Study. JAMA Ophthalmol. 2015 Aug. 1; 133(8):907-914.

30. Birch E E, Stager D R. The critical period for surgical treatment of dense congenital unilateral cataract. Invest Ophthalmol Vis Sci. 1996 Jul. 1; 37(8):1532-1538.

31. Lambert S R, Lynn M J, Reeves R, Plager D A, Buckley E G, Wilson M E. Is There a Latent Period for the Surgical Treatment of Children With Dense Bilateral Congenital Cataracts? J Am Assoc Pediatr Ophthalmol Strabismus. 2006 Feb. 1; 10(1):30-36.

32. Kaneko M, Fu Y, Stryker M P. Locomotion Induces Stimulus-Specific Response Enhancement in Adult Visual Cortex. J Neurosci. 2017 Mar. 29; 37(13):3532-3543. PMID: 28258167

33. Mimouni M, Shapira Y, Jadon J, Frenkel S, Blumenthal E Z. Assessing visual function behind cataract: preoperative predictive value of the Heine Lambda 100 retinometer. Eur J Ophthalmol. 2017 Aug. 30; 27(5):559-564. PMID: 28574134

34. Barrett B T, Davison P A, Eustace P. Clinical comparison of three techniques for evaluating visual function behind cataract. Eye. 1995 November; 9(6):722-727.

35. Halliday B L, Ross J E. Comparison of 2 interferometers for predicting visual acuity in patients with cataract. Br J Ophthalmol. 1983 May; 67(5):273-277. PMCID: PMC1040041

36. Mitchell D E, Kind P C, Sengpiel F, Murphy K. Short periods of concordant binocular vision prevent the development of deprivation amblyopia. Eur J Neurosci. 2006 May 1; 23(9):2458-2466.

37. Mitchell D E, Kind P C, Sengpiel F, Murphy K. Brief daily periods of binocular vision prevent deprivation-induced acuity loss. Curr Biol. 2003; 13(19):1704-1708.

38. Schwarzkopf D S, Vorobyov V, Mitchell D E, Sengpiel F. Brief daily binocular vision prevents monocular deprivation effects in visual cortex. Eur J Neurosci. 2007 Jan. 1; 25(1):270-280.

39. Mitchell D E, Sengpiel F, Hamilton D C, Schwarzkopf D S, Kennie J. Protection against deprivation amblyopia depends on relative not absolute daily binocular exposure. J Vis. 2011 Jun. 1; 11(7):13-13.

40. Sakai E, Bi H, Maruko I, Zhang B, Zheng J, Wensveen J, Harwerth R S, Smith E L, Chino Y M. Cortical Effects of Brief Daily Periods of Unrestricted Vision During Early Monocular Form Deprivation. J Neurophysiol. 2006 May 1; 95(5):2856-2865.

41. Stryker M P, Sherk H, Leventhal A G, Hirsch H V. Physiological consequences for the cat's visual cortex of effectively restricting early visual experience with oriented contours. J Neurophysiol. 1978 Jul. 1; 41(4):896-909.

42. Wang L V. Mechanisms of ultrasonic modulation of multiply scattered coherent light: an analytic model. Phys Rev Lett. 2001 Jul. 23; 87(4):043903. PMID: 11461618

43. Vellekoop I M, Mosk A P. Focusing coherent light through opaque strongly scattering media. Opt Lett. 2007 Aug. 15; 32(16):2309-2311. PMID: 17700768

44. Cui M. A high speed wavefront determination method based on spatial frequency modulations for focusing light through random scattering media. Opt Express. 2011 Feb. 14; 19(4):2989-2995. PMID: 21369123

45. Popoff S M, Lerosey G, Carminati R, Fink M, Boccara A C, Gigan S. Measuring the transmission matrix in optics: an approach to the study and control of light propagation in disordered media. Phys Rev Lett. 2010 Mar. 12; 104(10): 100601. PMID: 20366410

46. Yaqoob Z, Psaltis D, Feld M S, Yang C. OPTICAL PHASE CONJUGATION FOR TURBIDITY SUPPRESSION IN BIOLOGICAL SAMPLES. Nat Photonics. 2008; 2(2):110-115. PMCID: PMC2688902

47. Beckwith P H, McMichael I, Yeh P. Image distortion in multimode fibers and restoration by polarization-preserving phase conjugation. Opt Lett. 1987 Jul. 1; 12(7):510-512. PMID: 19741781

48. Cui M, McDowell E J, Yang C. An in vivo study of turbidity suppression by optical phase conjugation (TSOPC) on rabbit ear. Opt Express. 2010 Jan. 4; 18(1):25-30. PMCID: PMC3369536

49. Yariv A. Phase conjugate optics and real-time holography. IEEE J Quantum Electron. 1978 September; 14(9): 650-660.

50. He G. Optical phase conjugation: principles, techniques, and applications. Prog Quantum Electron. 2002 May; 26(3):131-191.

51. Cui M, Yang C. Implementation of a digital optical phase conjugation system and its application to study the robustness of turbidity suppression by phase conjugation. Opt Express. 2010 Feb. 15; 18(4):3444-3455. PMCID: PMC3378352

52. Wang Y M, Judkewitz B, Dimarzio C A, Yang C. Deep-tissue focal fluorescence imaging with digitally time-reversed ultrasound-encoded light. Nat Commun. 2012 Jun. 26; 3:928. PMCID: PMC3621452

53. Si K, Fiolka R, Cui M. Breaking the spatial resolution barrier via iterative sound-light interaction in deep tissue microscopy. Sci Rep. 2012; 2:748. PMCID: PMC3475990

54. Judkewitz B, Wang Y M, Horstmeyer R, Mathy A, Yang C. Speckle-scale focusing in the diffusive regime with time-reversal of variance-encoded light (TROVE). Nat Photonics. 2013 Apr. 1; 7(4):300-305. PMCID: PMC3692396

55. Vellekoop I M, Cui M, Yang C. Digital optical phase conjugation of fluorescence in turbid tissue. Appl Phys Lett. 2012 Aug. 20; 101(8):81108. PMCID: PMC3436909

56. Hsieh C-L, Pu Y, Grange R, Laporte G, Psaltis D. Imaging through turbid layers by scanning the phase conjugated second harmonic radiation from a nanoparticle. Opt Express. 2010 Sep. 27; 18(20):20723-20731. PMID: 20940968

57. Yu Z, Huangfu J, Zhao F, Xia M, Wu X, Niu X, Li D, Lai P, Wang D. Time-reversed magnetically controlled perturbation (TRMCP) optical focusing inside scattering media. Sci Rep. 2018 Feb. 13; 8(1):2927. PMCID: PMC5811554

58. Ruan H, Haber T, Liu Y, Brake J, Kim J, Berlin J M, Yang C. Focusing light inside scattering media with magnetic-particle-guided wavefront shaping. Optica. 2017 Nov. 20; 4(11):1337-1343.

59. Ruan H, Jang M, Yang C. Optical focusing inside scattering media with time-reversed ultrasound microbubble encoded light. Nat Commun. 2015 Nov. 24; 6:8968. PMCID: PMC4673 873

60. Yang J, Shen Y, Liu Y, Hemphill A S, Wang L V. Focusing light through scattering media by polarization modulation based generalized digital optical phase conjugation. Appl Phys Lett. 2017 Nov. 13; 111(20):201108. PMCID: PMC5690666

61. Wang L V, Wu H. Biomedical Optics: Principles and Imaging. John Wiley & Sons; 2012.

62. Shen Y, Liu Y, Ma C, Wang L V. Focusing light through biological tissue and tissue-mimicking phantoms up to 9.6 cm in thickness with digital optical phase conjugation. J Biomed Opt. 2016 Aug. 1; 21(8):85001. PMCID: PMC4982119

63. Liu Y, Ma C, Shen Y, Wang L V. Bit-efficient, sub-millisecond wavefront measurement using a lock-in camera for time-reversal based optical focusing inside scattering media. Opt Lett. 2016 Apr. 1; 41(7):1321-1324. PMCID: PMC4874255

64. Shen Y, Liu Y, Ma C, Wang L V. Sub-Nyquist sampling boosts targeted light transport through opaque scattering media. Optica. 2017 Jan. 20; 4(1):97-102. PMCID: PMC5493046

65. American National Standard: for Ophthalmics—Light Hazard Protection for Ophthalmic Instruments. American National Standards Institute; 2016 March. Report No.: ANSI Z80.36-2016.

66. Delori F C, Webb R H, Sliney D H. Maximum permissible exposures for ocular safety (ANSI 2000), with emphasis on ophthalmic devices. JOSA A. 2007; 24(5): 1250-1265.

67. Sliney D H, Mellerio J, Gabel V-P, Schulmeister K. What is the meaning of threshold in laser injury experiments? Implications for human exposure limits. Health Phys. 2002 March; 82(3):335-347. PMID: 11845836

68. Sliney D H, Mellerio J. Safety with Lasers and Other Optical Sources: A Comprehensive Handbook. Springer Science & Business Media; 2013.

69. Brown A M, Dobson V, Maier J. Visual acuity of human infants at scotopic, mesopic and photopic luminances. Vision Res. 1987; 27(10):1845-1858. PMID: 3445474

70. Norcia A M, Tyler C W, Hamer R D. Development of contrast sensitivity in the human infant. Vision Res. 1990; 30(10):1475-1486. PMID: 2247957

71. Brown A M, Lindsey D T, Cammenga J G, Giannone P J, Stenger M R. The Contrast Sensitivity of the Newborn Human Infant. Invest Ophthalmol Vis Sci. 2015 January; 56(1):625. PMID: 25564453

72. Hunter J J, Morgan J I W, Merigan W H, Sliney D H, Sparrow J R, Williams D R. The susceptibility of the retina to photochemical damage from visible light. Prog Retin Eye Res. 2012 January; 31(1):28-42.

73. Robert Phillips, Ph.D; Food and Drug Administration. Guidance for Industry and FDA Staff Information for Manufacturers Seeking Marketing Clearance of Diagnostic Ultrasound Systems and Transducers. 2008 September p. 62.

74. Szabo T L. Diagnostic Ultrasound Imaging: Inside Out. Elsevier; 2004.

75. Abbott J G. Rationale and derivation of MI and TI—a review 1. Ultrasound Med Biol. 1999; 25(3):431-441.

76. Le Clerc F, Collot L, Gross M. Numerical heterodyne holography with two-dimensional photodetector arrays. Opt Lett. 2000 May 15; 25(10):716-718. PMID: 18064161

77. Amin V. Ultrasonic attenuation estimation for tissue characterization. Retrosp Theses Diss [Internet]. 1989 Jan. 1; Available from: https://lib.dr.iastate.edu/rtd/17318

78. Goodman J W. Speckle Phenomena in Optics: Theory and Applications. Roberts and Company Publishers; 2007.

79. Hubel D H, Wiesel T N. Receptive fields, binocular interaction and functional architecture in the cat's visual cortex. J Physiol. 1962 January; 160(1):106. PMID: 14449617

80. Hirsch H V. Visual perception in cats after environmental surgery. Exp Brain Res. 1972; 15(4):405-423. PMID: 5079472

81. Daw N W, Wyatt H J. Kittens reared in a unidirectional environment: evidence for a critical period. J Physiol. 1976 May; 257(1):155-170. PMCID: PMC1309349

82. Heinrich S P, Bock C M, Bach M. Imitating the effect of amblyopia on VEP-based acuity estimates. Doc Ophthalmol. 2016 December; 133(3):183-187.

83. Wandell B A. Foundations of Vision. 1 edition. Sunderland, Mass.: Sinauer Associates Inc; 1995.

84. Liu C, Ma Y, Shen L. Y. Wang, Bit-efficient, sub-millisecond wavefront measurement using a lock-in camera for time-reversal based optical focusing inside scattering media, Opt. Lett. 2016; 41(7 SRC-GoogleScholar):1321-1324.

85. Trivedi R H, Wilson M E. Axial length measurements by contact and immersion techniques in pediatric eyes with cataract. Ophthalmology. 2011 March; 118(3):498-502. PMCID: PMC3052929

86. Weale R A. The post-mortem preservation of the transmissivity of the human crystalline lens. Exp Eye Res. 1985 Nov. 1; 41(5):655-659.

87. Weale R A. Transparency and power of post-mortem human lenses: Variation with age and sex. Exp Eye Res. 1983 May 1; 36(5):731-741.

88. Weale R A. Human lenticular fluorescence and transmissivity, and their effects on vision. Exp Eye Res. 1985 Oct. 1; 41(4):457-473.

89. Tsonis P A. Animal models in eye research. San Diego, Calif.: Elsevier/Academic Press; 2008.

90. Prevention of selenite cataract by vitamin C. Exp Eye Res. 1991 May 1; 52(5):563-568.

91. Kyselova Z. Different experimental approaches in modelling cataractogenesis: An overview of selenite-induced nuclear cataract in rats. Interdiscip Toxicol. 2010 March; 3(1):3. PMID: 21217865

92. Caixinha M, Amaro J, Santos M, Perdigao F, Gomes M, Santos J. In-Vivo Automatic Nuclear Cataract Detection and Classification in an Animal Model by Ultrasounds. IEEE Trans Biomed Eng. 2016 November; 63(11):2326-2335.

93. Peighambarzadeh S Z, Tavana M. Attenuation of experimental cataract by vitamin C in rabbits. 2014;

94. Parks M M, Johnson D A, Reed G W. Long-term visual results and complications in children with aphakia: A function of cataract type. Ophthalmology. 1993; 100(6):826-841.

95. Wilson M E, Trivedi R H, Morrison D G, Lambert S R, Buckley E G, Plager D A, Lynn M J. The Infant Aphakia Treatment Study: Evaluation of cataract morphology in eyes with monocular cataracts. J Am Assoc Pediatr Ophthalmol Strabismus. 2011 Oct. 1; 15(5):421-426.

96. Hwang H B, Kim H S. Phototoxic effects of an operating microscope on the ocular surface and tear film. Cornea. 2014 January; 33(1):82-90. PMID: 24310622

97. Aydin B, Dinç E, Yilmaz S N, Altiparmak U E, Yülek F, Ertekin S, Yilmaz M, Yakin M. Retinal endoilluminator toxicity of xenon and light-emitting diode (LED) light source: rabbit model. Cutan Ocul Toxicol. 2014 September; 33(3):192-196. PMID: 24147949

98. Werner L, Chang W, Haymore J, Haugen B, Romaniv N, Sandstedt C, Chang S, Mamalis N. Retinal safety of the irradiation delivered to light-adjustable intraocular lenses evaluated in a rabbit model. J Cataract Refract Surg. 2010 August; 36(8):1392-1397.

99. Wu J, Seregard S, Algvere P V. Photochemical Damage of the Retina. Sury Ophthalmol. 2006 Sep. 1; 51(5): 461-481. PMID: 16950247

100. de Smet M D, Mura M. Minimally invasive surgery—endoscopic retinal detachment repair in patients with media opacities. Eye. 2008 May; 22(5):662-665.

101. Ren H, Jiang R, Xu G, Chang Q, Lv J, Chen Q, Wang W. Endoscopy-assisted vitrectomy for treatment of severe endophthalmitis with retinal detachment. Graefes Arch Clin Exp Ophthalmol. 2013 Jul. 1; 251(7):1797-1800.

102. Smet M D D, Carlborg E A E. Managing Severe Endophthalmitis With The Use Of An Endoscope. Retina. 2005 Dec. 1; 25(8):976-980. PMID: 00006982-200512000-00004

103. Yoshitake S, Oh H, Kita M. Endoscope-assisted vitrectomy for retinal detachment in an eye with microcornea. Jpn J Ophthalmol. 2012 Nov. 1; 56(6):613-616.

104. Ben-nun J. Cornea sparing by endoscopically guided vitreoretinal surgery. Ophthalmology. 2001 August; 108(8): 1465-1470. PMID: 11470702

105. Lee S-M, Kim M-K, Oh J Y, Heo J-W, Shin M-S, Lee M-S, Wee W-R, Lee J-H. Endoscopic Vitrectomy Improves Outcomes of Seoul-type Keratoprosthesis Exchange in Rabbit Model. Invest Ophthalmol Vis Sci. 2008 Oct. 1; 49(10): 4407-4411.

106. Khraiche M L, Emam S E, Akinin A, Cauwenberghs G, Freeman W, Silva G A. Visual evoked potential characterization of rabbit animal model for retinal prosthesis research. 2013 35th Annu Int Conf IEEE Eng Med Biol Soc EMBC. 2013. p. 3539-3542.

107. Norcia A M, Appelbaum L G, Ales J M, Cottereau B R, Rossion B. The steady-state visual evoked potential in vision research: A review. J Vis [Internet]. 2015 [ cited 2018 Apr. 2]; 15(6). Available from: https://www-ncbi-nlm-nih-gov.ucsfidm.ocic.org/pmc/articles/PMC4581566/PMID: 26024451

108. Lanum J. The damaging effects of light on the retina. Empirical findings, theoretical and practical implications. Sury Ophthalmol. 1978 January; 22(4):221-249.

109. Bailey I L, Jackson A J. Changes in the clinical measurement of visual acuity. J Phys Conf Ser. 2016; 772(1):012046.

110. Consilium Ophthalmologicum Universale Visual Functions Committee, Visual Acuity Measurement Standard. Ital J Ophthalmol. 1988; 11:5-19.

111. Recommended stardard procedures for the clinical measurement and specification of visual acuity. Report of working group 39. Committee on vision. Assembly of Behavioral and Social Sciences, National Research Council, National Academy of Sciences, Washington, D.C. Adv Ophthalmol Fortschritte Augenheilkd Progres En Ophthalmol. 1980; 41:103-148. PMID: 7001873

112. Bailey I L, Lovie J E. New design principles for visual acuity letter charts. Am J Optom Physiol Opt. 1976 November; 53(11):740-745. PMID: 998716

113. Arditi A, Cagenello R. On the statistical reliability of letter-chart visual acuity measurements. Invest Ophthalmol Vis Sci. 1993 January; 34(1):120-129. PMID: 8425819

114. Aminoff M J, Goodin D S. Visual Evoked Potentials. [Review]. J Clin Neurophysiol. 1994 September; 11(5):493-499.

115. Taylor M J, McCulloch D L. Visual Evoked Potentials in Infants and Children. [Editorial]. J Clin Neurophysiol. 1992 July; 9(3):357-372.

116. Lauritzen L, Jørgensen M H, Michaelsen K F. Test-Retest Reliability of Swept Visual Evoked Potential Measurements of Infant Visual Acuity and Contrast Sensitivity. Pediatr Res. 2004 April; 55(4):701.

117. Infant VEP acuity measurements: Analysis of individual differences and measurement error. Electroencephalogr Clin Neurophysiol. 1985 Nov. 1; 61(5):359-369.

118. Brecelj J. From immature to mature pattern ERG and VEP. Doc Ophthalmol. 2003 Nov. 1; 107(3):215-224.

119. Fiorentini A, Pirchio M, Sandini G. Development of retinal acuity in infants evaluated with pattern electroretinogram. Hum Neurobiol. 1984; 3(2):93-95. PMID: 6746336

120. Fiorentini A, Pirchio M, Spinelli D. Development of retinal and cortical responses to pattern reversal in infants: A selective review. Behav Brain Res. 1983 October; 10(1):99-106.

121. Sokol S, Hansen V C, Moskowitz A, Greenfield P, Towle V L. Evoked Potential and Preferential Looking Estimates of Visual Acuity in Pediatric Patients. Ophthalmology. 1983 May; 90(5):552-562.

122. Sokol S. Abnormal evoked potential latencies in amblyopia. Br J Ophthalmol. 1983 May 1; 67(5):310-314. PMID: 6838802

123. Jeon J, Oh S, Kyung S. Assessment of visual disability using visual evoked potentials. BMC Ophthalmol. 2012; 12:36. PMID: 22866948

124. Sokol S, Bloom B. Visually evoked cortical responses of amblyopes to a spatially alternating stimulus. Invest Ophthalmol. 1973 December; 12(12):936-939. PMID: 4768599

125. Oner A, Coskun M, Evereklioglu C, Dogan H. Pattern VEP is a useful technique in monitoring the effectiveness of occlusion therapy in amblyopic eyes under occlusion therapy. Doc Ophthalmol. 2004 November; 109(3):223-227.

126. Allen R J, Speedwell L, Russell-Eggitt I. Long-term visual outcome after extraction of unilateral congenital cataracts [Internet]. Eye. 2009 [cited 2018 Jan. 10]. Available from: https://www.nature.com/articles/eye2009295

127. Chak M, Wade A, Rahi J S. Long-Term Visual Acuity and Its Predictors after Surgery for Congenital Cataract: Findings of the British Congenital Cataract Study. Invest Ophthalmol Vis Sci. 2006 Oct. 1; 47(10):4262-4269.

128. Rajavi Z, Mokhtari S, Sabbaghi H, Yaseri M. Long-term visual outcome of congenital cataract at a Tertiary Referral Center from 2004 to 2014. J Curr Ophthalmol. 2016 Jan. 13; 27(3-4):103-109. PMCID: PMC4881158

129. Shearer T R, Ma H, Fukiage C, Azuma M. Selenite nuclear cataract: review of the model. Mol Vis. 1997 Jul. 23; 3:8. PMID: 9238097

130. Lawwill T. Effects of prolonged exposure of rabbit retina to low-intensity light. Invest Ophthalmol Vis Sci. 1973 Jan. 1; 12(1):45-51.

131. U.S. Census Bureau QuickFacts: Los Angeles County, California [Internet]. [cited 2018 Apr. 4]. Available from: https://www.census.gov/quickfacts/fact/table/losangelescountycalifornia/PST045216

Conclusion

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A device for irradiating ocular tissue, comprising:
a transmitter of ultrasound capable of transmitting ultrasound forming a beacon comprising a focus of ultrasound behind an opacity in ocular tissue,
a source of electromagnetic radiation capable of transmitting electromagnetic radiation to the opacity, wherein the electromagnetic radiation is transmitted through the opacity and the beacon scatters the electromagnetic radiation transmitted through the opacity so as to form scattered electromagnetic radiation; and
a system generating output electromagnetic radiation, the system:
recording a recording of the scattered electromagnetic radiation transmitted through the opacity;
including a modulator modulating one or more output wavefronts of the output electromagnetic radiation, forming the output electromagnetic radiation having a field determined from the recording of the scattered electromagnetic radiation transmitted through the opacity; and
patterning the output electromagnetic radiation;
so that the output electromagnetic radiation is transmitted and focused through the opacity to the beacon on tissue, and the output electromagnetic radiation forms a patterned image on the ocular tissue.

2. The device of claim 1, wherein the ultrasound comprises an ultrasound frequency and the ultrasound frequency shifts the electromagnetic radiation transmitted through the opacity so as to form the scattered electromagnetic radiation comprising frequency shifted electromagnetic radiation.

3. The device of claim 2, wherein the system further comprises:
a detector outputting a signal comprising the recording in response to the scattered electromagnetic radiation received on the detector;
a computer connected to the detector and the modulator:
the computer determining a phase, an amplitude, or an amplitude and a phase of the output electromagnetic radiation from the recording; and
the modulator modulating the output electromagnetic radiation so that the output electromagnetic radiation has the phase, the amplitude, or the amplitude and the phase.

4. The device of claim 3, wherein:
the modulator comprises pixels, wherein:
the pixels have variable transmissivity, reflectivity, or emission so as to modulate an intensity of the output electromagnetic radiation transmitted from the pixels,
the computer controls the transmissivity, reflectivity, or emission of each of the pixels so as to form a varying intensity comprising a stimulating pattern capable of stimulating nerves on retinal tissue, and
the beacon is on the retinal tissue.

5. The device of claim 4, wherein:
the computer determines, from the signal, values representing a phase, an amplitude, or a phase and an amplitude of the scattered electromagnetic radiation at spatial locations associated with the stimulating pattern; and the computer determines the phase, the amplitude, or the amplitude and the phase of the output electromagnetic radiation from the values.

6. The device of claim 5, wherein the computer temporally controls the transmissivity, the reflectivity, or the emission of each of the pixels so that all points or regions of the stimulating pattern are transmitted from the modulator sequentially in time.

7. The device of claim 5, wherein:
the computer determines, from the signal, the values representing the phase, an amplitude, or the phase and the amplitude of the scattered electromagnetic radiation for a subset of the spatial locations associated with the stimulating pattern; and
the computer uses an optical memory effect to calculate the phase and/or amplitude for neighboring points in the stimulating pattern by adding different phase gradients.

8. The device of claim 4, wherein the stimulating pattern comprises a line.

9. The device of claim 4, wherein the stimulating pattern comprises a pair of lines moving closer together so as to measure visual acuity.

10. The device of claim 3, wherein:
the detector comprises a wavefront sensor measuring a wavefront for each spatial location in the scattered electromagnetic radiation associated with the patterned image comprising a stimulation pattern;
the computer synthesizes the one or more output wavefronts of the output electromagnetic radiation using the wavefronts; and
the modulator performs the patterning modulating the output electromagnetic radiation so as to transmit the stimulation pattern to the beacon.

11. The device of claim 10, wherein:
the modulator comprises pixels that are sequentially modulated so as to scan the output electromagnetic radiation representing different points in the stimulation pattern across retinal tissue within a duration of persistence of vision so that a subject perceives the stimulation pattern, wherein the beacon is on the retinal tissue, and/or
the computer uses an optical memory effect to determine the output wavefronts for neighboring points in the stimulation pattern by adding different phase gradients so as to reduce a number of the wavefronts measured by the wavefront sensor.

12. The device of claim 2, wherein the modulating forms the output electromagnetic radiation comprising a phase conjugate of the scattered electromagnetic radiation transmitted through the opacity.

13. The device of claim 1, wherein:
the ocular tissue comprises lens tissue comprising cataractous tissue or other light scattering media intersecting with an optical axis of an eye.

14. The device of claim 13, wherein the beacon is positioned on the ocular tissue comprising retinal tissue.

15. The device of claim 1, wherein the beacon is a non-invasive guide star and any heating of the tissue is negligible.

16. A method of irradiating ocular tissue, comprising:
providing a beacon behind an opacity in ocular tissue so as to scatter electromagnetic radiation transmitted through the opacity and form scattered electromagnetic radiation, wherein the beacon comprises a focus of ultrasound;
recording a recording of the scattered electromagnetic radiation transmitted through the opacity;
modulating a wavefront of output electromagnetic radiation so as to form the output electromagnetic radiation having a field determined from the recording of the scattered electromagnetic radiation transmitted through the opacity; and
patterning the output electromagnetic radiation, wherein the output electromagnetic radiation is transmitted and focused through the opacity to the beacon on tissue, forming a patterned image on the tissue.

17. The method of claim 16, further comprising:
transmitting the ultrasound so as to form the beacon comprising the focus of the ultrasound, wherein the ultrasound comprises an ultrasound frequency and the ultrasound frequency shifts the electromagnetic radiation transmitted through the opacity so as to form the scattered electromagnetic radiation comprising frequency shifted electromagnetic radiation.

18. The method of claim 17, wherein the modulating forms the output electromagnetic radiation comprising a phase conjugate of the scattered electromagnetic radiation transmitted through the opacity.

19. The method of claim 18, wherein:
the modulating comprises the patterning forming the output electromagnetic radiation comprising the patterned image comprising a stimulating pattern useful for stimulating nerves in retinal tissue, and
the beacon is on the tissue comprising the retinal tissue.

20. A device for irradiating ocular tissue, comprising:
a source of electromagnetic radiation capable of transmitting electromagnetic radiation to an opacity in ocular tissue;
a transmitter of ultrasound capable of transmitting ultrasound forming a beacon comprising a focus of the ultrasound behind the opacity, the beacon scattering the electromagnetic radiation transmitted through the opacity in the ocular tissue so as to form scattered electromagnetic radiation;
a wavefront sensor measuring at least a phase or an amplitude of the scattered electromagnetic radiation transmitted through the opacity; and
a computer mapping optical properties at different spatial locations across the ocular tissue using the at least one of the phase or the amplitude.

21. The device of claim 20, wherein the electromagnetic radiation has the phase and the amplitude selected to optically determine the optical properties comprising optical scattering of the ocular tissue comprising corneal tissue or lens tissue.

* * * * *